(12) United States Patent
Gawlick

(10) Patent No.: US 8,374,988 B2
(45) Date of Patent: Feb. 12, 2013

(54) COMPLEX ALERT RULES FOR A MEDICAL PERSONNEL ALERT SYSTEM

(75) Inventor: Ute Gawlick, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 543 days.

(21) Appl. No.: 12/707,925

(22) Filed: Feb. 18, 2010

(65) Prior Publication Data
US 2011/0202490 A1 Aug. 18, 2011

(51) Int. Cl.
*G06F 17/00* (2006.01)
*G06N 5/02* (2006.01)

(52) U.S. Cl. ........... 706/47; 706/45; 706/52; 706/62; 600/300; 600/301

(58) Field of Classification Search .......... None
See application file for complete search history.

(56) References Cited

U.S. PATENT DOCUMENTS

| | | | |
|---|---|---|---|
| 3,742,937 A | 7/1973 | Manuel et al. | |
| 7,003,529 B2 | 2/2006 | Lusen et al. | |
| 7,551,078 B2 | 6/2009 | Carlson et al. | |
| 7,596,538 B1 | 9/2009 | Owen et al. | |
| 2005/0060186 A1* | 3/2005 | Blowers et al. | 705/2 |
| 2006/0025657 A1 | 2/2006 | Rosenfeld et al. | |
| 2006/0049936 A1 | 3/2006 | Collins et al. | |
| 2007/0013651 A1 | 1/2007 | Depue et al. | |
| 2007/0219830 A1* | 9/2007 | Warner et al. | 705/3 |
| 2007/0294360 A1 | 12/2007 | Ebling et al. | |
| 2008/0004906 A1* | 1/2008 | Klass et al. | 705/2 |
| 2008/0058773 A1 | 3/2008 | John | |
| 2008/0061961 A1* | 3/2008 | John | 340/539.12 |
| 2008/0071314 A1* | 3/2008 | John | 607/2 |
| 2008/0097553 A1 | 4/2008 | John | |
| 2008/0139898 A1* | 6/2008 | Johnson et al. | 600/301 |
| 2008/0162254 A1* | 7/2008 | Herger et al. | 705/9 |
| 2009/0054735 A1 | 2/2009 | Higgins et al. | |
| 2009/0138289 A1 | 5/2009 | Klass et al. | |
| 2009/0187419 A1 | 7/2009 | Renganathan et al. | |
| 2010/0050085 A1* | 2/2010 | Blike et al. | 715/738 |

OTHER PUBLICATIONS

Non-Final Office Action issued by the USPTO in U.S. Appl. No. 12/707,982, filed Aug. 20, 2012, 8 pages.
Non-Final Office Action issued by the USPTO in U.S. Appl. No. 12/707,933, filed Jun. 26, 2012, 24 pages.

(Continued)

*Primary Examiner* — Omar Fernandez Rivas
(74) *Attorney, Agent, or Firm* — Bell & Manning, LLC

(57) ABSTRACT

A method, a system, and a computer-readable medium are provided for generating a complex alert. Values of a plurality of physiological characteristics of a patient are received. The received values are compared to a complex alert rule associated with a medical condition. The complex alert rule includes a plurality of alert rules, wherein each alert rule includes an indicator of a physiological characteristic of a patient associated with the alert rule and a condition priority associated with an urgency of the alert rule. The complex alert rule also includes a trigger rule. The trigger rule includes a plurality of rules wherein each rule includes a number of satisfied alert rules for each value of the condition priority. A number of alert rules of the plurality of alert rules that are satisfied is determined for each condition priority of the complex alert rule based on the comparison. A complex alert is generated if the determined number of alert rules for a condition priority satisfies the trigger rule of the complex alert rule.

20 Claims, 25 Drawing Sheets

OTHER PUBLICATIONS

Ute Gawlick, A Novel Approach to ICU Surveillance and Prediction of Disease, Oracle Presentation, Salt Lake City, UT, Aug. 14, 2009, 22 pages.

Guerra et al., An Integrated Data Management Approach to Manage Health Care Data, DEBS Poster Presentation, Jul. 6-9, 2009, Nashville, TN., 1 page.

Diogo Guerra, An Integrated Data Management Approach to Manage Health-Care Sensor Data, Oracle Seminar, Jul. 10, 2009, Redwood Shores, CA., 32 pages.

International Search Report and Written Opinion received in PCT/US2011/025385, Jul. 19, 2011.

Guerra et al., An integrated data management approach to manage health care data, Proceedings of the Third ACM International Conference on Distributed Event-Based Systems, DEBS '09, Jan. 1, 2009, pp. 1-2.

Oracle Database Rules Manager and Expression Filter Developers Guide, Jul. 1, 2007, pp. 15-24.

\* cited by examiner

Fig. 11

| Physiological Characteristic Indicator | Minimum Range Values | | | | Maximum Range Values | | | |
|---|---|---|---|---|---|---|---|---|
| | Critical | Serious | Guarded | Normal | Normal | Guarded | Serious | Critical |
| ... | | | | | | | | |
| TEMPERATURE | 34.5 | 36 | 37 | 37.0 | 38.4 | 38.4 | 40 | 42 |
| HEART RATE | 40 | 50 | 60 | 60 | 100 | 100 | 125 | 150 |
| SYSTOLIC BLOOD PRESSURE | 70 | 80 | 90 | 90 | 140 | 140 | 160 | 190 |
| DIASTOLIC BLOOD PRESSURE | 40 | 50 | 60 | 60 | 90 | 90 | 100 | 110 |
| MEAN ARTERIAL PRESSURE | 60 | 65 | 70 | 70 | 105 | 105 | 110 | 115 |
| RESPIRATORY RATE | 8 | 10 | 14 | 14 | 26 | 26 | 30 | 35 |
| OXYGEN SATURATION | 80 | 85 | 90 | 90 | 100 | | | |
| WEIGHT | | | | | | | | |
| EKG | | | | | | | | |
| CARDIAC OUTPUT | 3 | | 4 | 4.0 | 6.0 | 6 | | 8 |
| CARDIAC INDEX | 2.2 | | 2.6 | 2.6 | 4.2 | 4.2 | | 6 |
| SYSTEMIC VASCULAR RESISTANCE | 600 | 700 | 800 | 800 | 1200 | 1200 | 1400 | 1600 |
| PULMONARY CAPILLARY WEDGE PRESSURE | | | | 4 | 12 | | | |
| INTRA ABDOMINAL PRESSURE | | | | 5 | 15 | 15 | 20 | 30 |
| ... | | | | | | | | |

1100

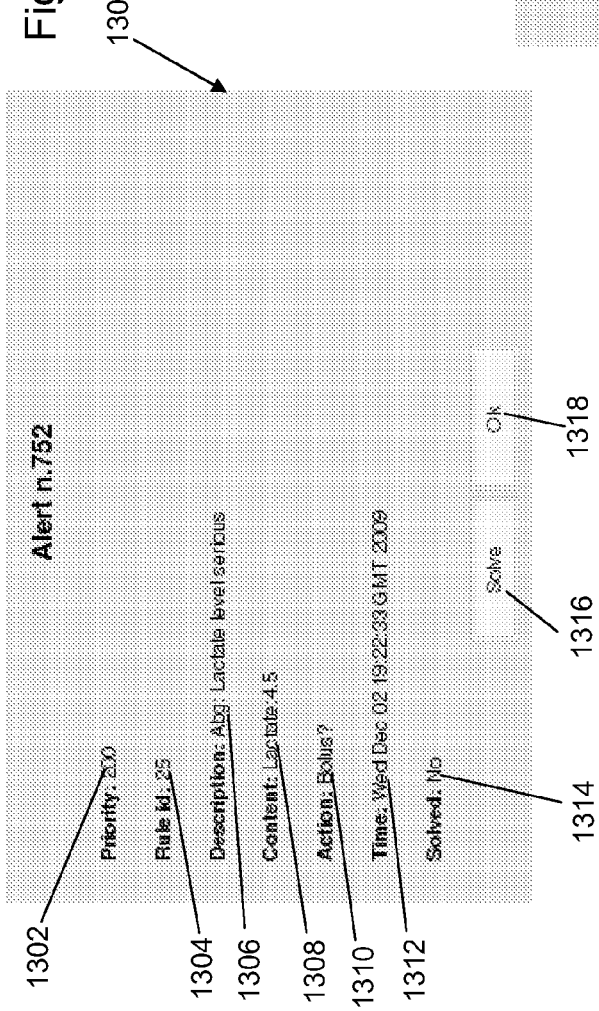

| Group | Color | Description | Delay |
|---|---|---|---|
| 500 | ORANGE | MAP in critical or serious range >30min | Immediate |
| 500 | ORANGE | MAP in critical or serious range >30min | Immediate |
| 500 | ORANGE | DROP of MAP in critical or serious range >30min | Immediate |
| 501 | ORANGE | SBP in critical or serious range >30min | Immediate |
| 501 | ORANGE | SBP in critical or serious range >30min | Immediate |
| 501 | ORANGE | DROP of SBP in critical or serious range >30min | Immediate |
| 502 | ORANGE | DBP in critical or serious range >30min | Immediate |
| 502 | ORANGE | DBP in critical or serious range >30min | Immediate |
| 502 | ORANGE | DROP of DBP in critical or serious range >30min | Immediate |

Fig. 22

| Patient | Name | Age | Sex | Alerts | Complex Alerts | Predictions |
|---|---|---|---|---|---|---|
| 12345670 | Jane Doe | 82 | f | 12 | 0 | 0 |
| 12345679 | John Doe | 29 | m | 0 | 0 | 0 |
| 12345678 | Trauma Alpha | 39 | f | 0 | 0 | 0 |

Fig. 26

Medications report 2900

| Medication | Dose | Route | Schedule | Indication | Last Given | Start Date | Stop Date | Holding Parameters |
|---|---|---|---|---|---|---|---|---|
| Zosyn | 3.375 gm | IV | Q6hrs | Infection | 06/01 18:00 | 06/01 00:00 | 06/05 00:00 | none |
| Metoprolol | 2 mg | IV | Q6hrs | Cardiac Home Med | 06/01 18:00 | 06/01 00:00 | 06/10 00:00 | SBP<65 |
| Zofran | 4 mg | IV | Q4hrs PRN | Nausea | 06/02 14:00 | 05/30 00:00 | 06/05 00:00 | none |
| Morphine | 1 mg | IV | Q2hrs PRN | Pain | 06/02 16:00 | 06/01 00:00 | 06/05 00:00 | none |

COMPLEX ALERT RULES FOR A MEDICAL PERSONNEL ALERT SYSTEM

BACKGROUND

Modern medical institutions have electronic devices that continuously monitor the vital signs of patients such as heart rate, respiratory rate, cardiac rhythm, blood pressure, oxygen saturation, and many other patient physiological characteristics. The electronic devices may be set to trigger alerts for critical values that are above and/or below predefined thresholds. Because the predefined thresholds are static, the electronic devices alert the doctors, nurses, and/or other medical personnel for the same critical values regardless of the patient condition, the patient demographics, any previous alarm history, etc. Thus, for example, the electronic devices typically do not distinguish between:

A patient with a cardiac condition and a patient without a cardiac condition;
 A male baby with a high heart rate and a female senior with a high heart rate; and/or
 A patient that started to have a high fever and a patient that has had a high fever for a period of time, for example, more than 30 minutes.

Ignoring these types of differences between patients may result in missed alarms, a high rate of false alarms, and alert fatigue, which may cause the medical staff to ignore alerts.

SUMMARY

In an example embodiment, a method for generating a complex alert is provided. Values of a plurality of physiological characteristics of a patient are received. The received values are compared to a complex alert rule associated with a medical condition. The complex alert rule includes a plurality of alert rules, wherein each alert rule includes an indicator of a physiological characteristic of a patient associated with the alert rule and a condition priority associated with an urgency of the alert rule. The complex alert rule also includes a trigger rule. The trigger rule includes a plurality of rules wherein each rule includes a number of satisfied alert rules for each value of the condition priority. A number of alert rules of the plurality of alert rules that are satisfied is determined for each condition priority of the complex alert rule based on the comparison. A complex alert is generated if the determined number of alert rules for a condition priority satisfies the trigger rule of the complex alert rule.

In another example embodiment, a computer-readable medium is provided having stored thereon computer-readable instructions that when executed by a computing device, cause the computing device to perform the method of generating a complex alert.

In yet another example embodiment, a system is provided. The system includes, but is not limited to, a processor and the computer-readable medium operably coupled to the processor. The computer-readable medium has instructions stored thereon that when executed by the processor, cause the system to perform the method of generating a complex alert.

The foregoing summary is illustrative only and is not intended to be in any way limiting. Other principal features and advantages of the invention will become apparent to those skilled in the art upon review of the following drawings, the detailed description, and the appended claims.

BRIEF DESCRIPTION OF THE DRAWINGS

Example embodiments will hereafter be described with reference to the accompanying drawings, wherein like numerals denote like elements. The drawings depict example embodiments in accordance with the disclosure and are, therefore, not to be considered limiting of its scope.

FIGS. 6-31 depict user interface windows of the medical alert application of FIG. 5 in accordance with an example embodiment.

DETAILED DESCRIPTION

Figure 1:
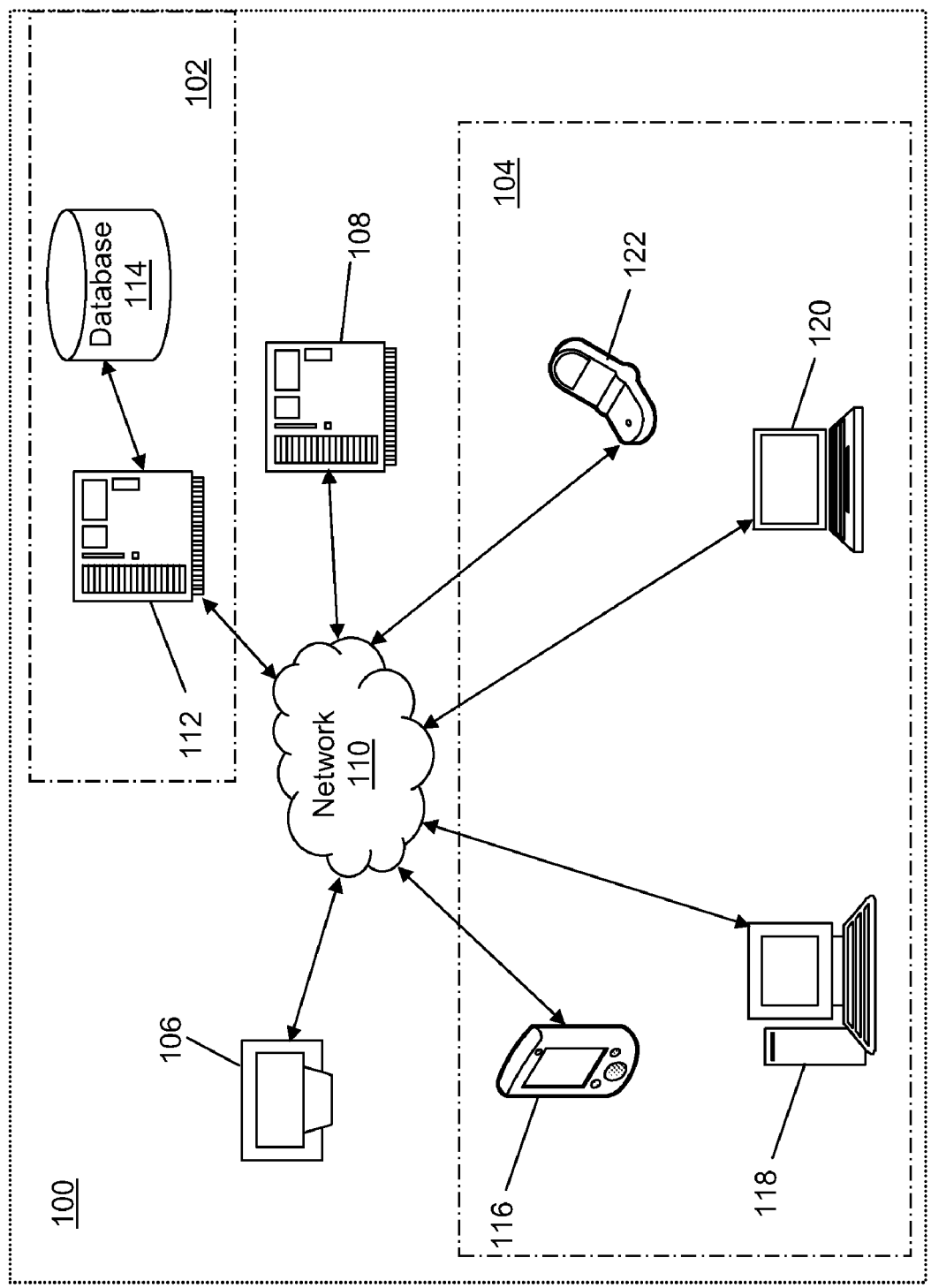
FIG. 1 depicts a block diagram of a medical alert system in accordance with an example embodiment.

With reference to FIG. 1, a block diagram of a medical alert system 100 is shown in accordance with an example embodiment. Medical alert system 100 may include a data processing system 102, a medical personnel alert system 104, a patient monitor system 106, a data generation system 108, and a network 110. Network 110 may include one or more networks of the same or different types. Network 110 can be any type of wired and/or wireless public or private network including a cellular network, a local area network, a wide area network such as the Internet, etc. Network 110 further may be comprised of sub-networks and consist of any number of devices.

Data processing system 102 may include a server computing device 112 and a database 114. Server computing device 112 may be a computer of any form factor. Server computing device 112 includes or can access database 114 either through a direct connection or through a second network. Database 114 is a data repository for medical alert system 100. Database 114 may include a plurality of databases that may be organized into multiple database tiers to improve data management and access. Database 114 may utilize various database technologies and a variety of different formats as known to those skilled in the art including a file system, a relational database, a system of tables, a structured query language database, etc. Database 114 may be implemented as a single database or as multiple databases stored in different storage locations distributed over the Internet or other heterogeneous storage infrastructures.

In an example embodiment, database 114 is implemented using Oracle® technologies such as Total Recall, Continuous Query Notification, Rules Manager, Data Mining, etc. Oracle® Total Recall is a technology developed to transparently handle the versioning of records. Using Oracle® Total Recall, database 114 can automatically maintain all versions of a record and corresponding timestamps. Using Oracle® Continuous Query Notification, database 114 can notify clients about new, changed, or deleted data. Using Oracle® Rules Manager, a rules engine is included in database 114. The rules engine works based on events represented by objects which are matched to previously defined rules. Rules can identify a sequence of events, patterns based on aggregations, non occurrence of events, etc. Using Oracle® Data Mining, a full data mining engine is embedded in database 114. In other embodiments, database 114 may be implemented using additional and/or different database technologies.

Medical personnel alert system 104 may include one or more computing devices. The one or more computing devices send and receive signals through network 110 to/from another of the one or more computing devices, to/from data processing system 102, to/from patient monitor system 106, and/or to/from data generation system 108. Medical personnel alert system 104 can include any number and type of computing devices that may be organized into subnets. The one or more computing devices may include computers of any form factor such as a personal digital assistant 116, a desktop 118, a laptop 120, an integrated messaging device, a cellular telephone 122, a smart phone, a pager, etc. Medical personnel alert system 104 may include additional types of devices. The one or more computing devices communicate using various transmission media that may be wired or wireless as known to those skilled in the art. The one or more computing devices may communicate information as peers in a peer-to-peer network using network 110. Medical personnel may use a computing device of the one or more computing devices to receive alerts related to patients, to check a status of a patient, to update a status of the patient, etc.

Patient monitor system 106 includes one or more electronic devices that continuously, periodically, and/or upon request monitor the physiological characteristics of patients such as heart rate, respiratory rate, cardiac rhythm, blood pressure, oxygen saturation, blood chemistry, etc. Some or all of the various electronic devices that makeup patient monitor system 106 may be connected to network 110 for the transmission of data, for example, for storage in database 114. Additionally, some or all of the various systems that makeup patient monitor system 106 may not be connected to network 110 for the transmission of the data. Instead, when an electronic device is not connected to network 110, the data may be manually provided to data processing system 102. For example, the data may be scanned or otherwise stored on electronic media such as a compact disk (CD), digital versatile disk (DVD), a smart card, a flash memory device, etc. After receiving the data, data processing system 102 may initiate processing of the data automatically or under control of an operator of server computing device 112.

Data generation system 108 generates data related to a patient in two-dimensions, three-dimensions, four-dimensions, etc. The source of and the dimensionality of the data is not intended to be limiting. In an example embodiment, the data is obtained from a medical imaging system such as a magnetic resonance imaging device, a computed tomography scanner, an ultrasound machine, an X-ray machine, etc., from a sensor associated with measuring a physiological characteristic of a patient such as a temperature, a blood pressure, a heart rate, blood chemistry, a respiratory rate, a heart state or condition, an intra-abdominal pressure, etc., from medical personnel evaluating and treating the patient, etc. Thus, data generation system 108 may include a medical imaging system such as a magnetic resonance imaging device, a computed tomography scanner, a sensor system, a computing device of any form factor used by medical personnel to capture patient physiological characteristics, etc.

Some or all of the various systems that makeup data generation system 108 may be connected to network 110 for the transmission of data, for example, for storage in database 114. Additionally, some or all of the various systems that makeup data generation system 108 may not be connected to network 110 for the transmission of the data. Instead, when a system is not connected to network 110, the data may be manually provided to data processing system 102. For example, the data may be scanned or otherwise stored on electronic media such as a CD, DVD, a smart card, a flash memory device, etc. After receiving the data, data processing system 102 may initiate processing of the data automatically or under control of an operator of server computing device 112.

The components of medical alert system 100 may be positioned in a single location, a single facility, and/or may be remote from one another. The components of medical alert system 100 may be integrated into a single system. One or more of the components of medical alert system 100 may be connected directly, for example, using a cable for transmitting information between systems. One or more of the components of medical alert system 100 may be connected using network 110. One or more of the components of medical alert system 100 may not be connected. Instead, the data acquired may be manually provided to data processing system 102.

Figure 2:
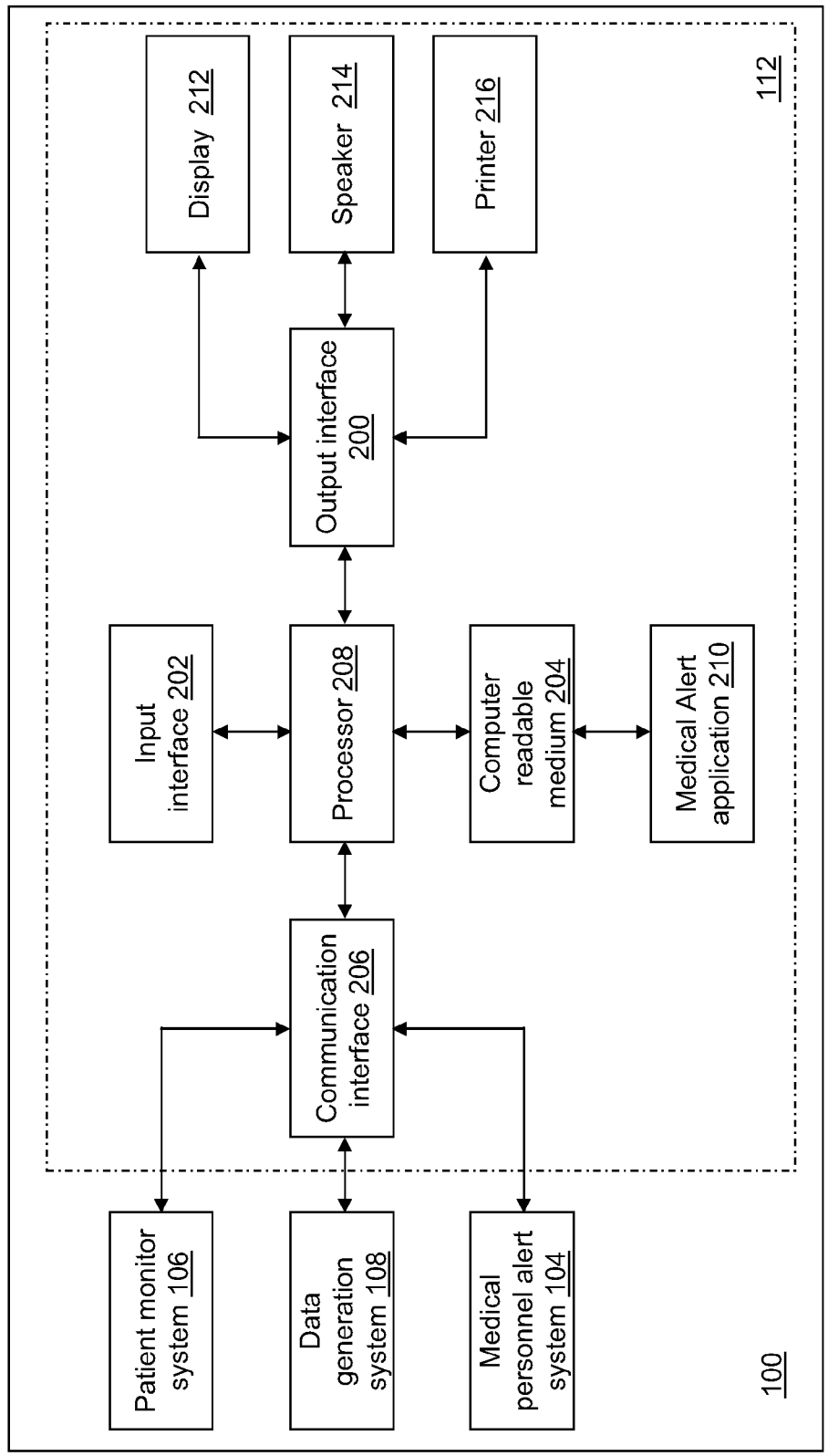
FIG. 2 depicts a block diagram of a server computing device of the medical alert system of FIG. 1 in accordance with an example embodiment.

With reference to FIG. 2, a block diagram of server computing device 112 is shown in accordance with an example embodiment. Server computing device 112 may include an output interface 200, an input interface 202, a computer-readable medium 204, a communication interface 206, a processor 208, a medical alert application 210, a display 212, a speaker 214, and a printer 216. Different and additional components may be incorporated into server computing device 112.

Output interface 200 provides an interface for outputting information for review by a user of server computing device 112. For example, output interface 200 may include an interface to display 212, speaker 214, printer 216, etc. Display 212 may be a thin film transistor display, a light emitting diode display, a liquid crystal display, or any of a variety of different displays known to those skilled in the art. Speaker 214 may be any of a variety of speakers as known to those skilled in the art. Printer 216 may be any of a variety of printers as known to those skilled in the art. Server computing device 112 may have one or more output interfaces that use the same or a different interface technology. Display 212, speaker 214, and/or printer 216 further may be accessible to server computing device 112 through communication interface 206.

Input interface 202 provides an interface for receiving information from the user for entry into server computing device 112 as known to those skilled in the art. Input interface 202 may use various input technologies including, but not limited to, a keyboard, a pen and touch screen, a mouse, a track ball, a touch screen, a keypad, one or more buttons, etc. to allow the user to enter information into server computing device 112 or to make selections presented in a user interface displayed on display 212. The same interface may support both input interface 202 and output interface 200. For example, a touch screen both allows user input and presents output to the user. Server computing device 112 may have one or more input interfaces that use the same or a different input interface technology.

Computer-readable medium 204 is an electronic holding place or storage for information so that the information can be accessed by processor 208 as known to those skilled in the art. Computer-readable medium 204 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Server computing device 112 may have one or more computer-readable media that use the same or a different memory media technology.

Server computing device 112 also may have one or more drives that support the loading of a memory media such as a CD or DVD. Computer-readable medium 204 may provide the electronic storage medium for database 114.

Communication interface 206 provides an interface for receiving and transmitting data between devices using various protocols, transmission technologies, and media as known to those skilled in the art. Communication interface 206 may support communication using various transmission media that may be wired or wireless. Server computing device 112 may have one or more communication interfaces that use the same or a different communication interface technology. Data and messages may be transferred between data processing system 102 and medical personnel alert system 104, patient monitor system 106, and/or data generation system 108 using communication interface 206.

Processor 208 executes instructions as known to those skilled in the art. The instructions may be carried out by a special purpose computer, logic circuits, or hardware circuits. Thus, processor 208 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 208 executes an instruction, meaning that it performs/controls the operations called for by that instruction. Processor 208 operably couples with output interface 200, with input interface 202, with computer-readable medium 204, and with communication interface 206 to receive, to send, and to process information. Processor 208 may retrieve a set of instructions from a permanent memory device and copy the instructions in an executable form to a temporary memory device that is generally some form of RAM. Server computing device 112 may include a plurality of processors that use the same or a different processing technology.

Medical alert application 210 performs operations associated with alerting medical personnel concerning a condition of a patient, with allowing medical personnel to check a status of a patient and/or to update a status of the patient, etc. Some or all of the operations described herein may be embodied in medical alert application 210. The operations may be implemented using hardware, firmware, software, or any combination of these methods. With reference to the example embodiment of FIG. 2, medical alert application 210 is implemented in software (comprised of computer-readable and/or computer-executable instructions) stored in computer-readable medium 204 and accessible by processor 208 for execution of the instructions that embody the operations of medical alert application 210. Medical alert application 210 may be written using one or more programming languages, assembly languages, scripting languages, etc.

Medical alert application 210 may be implemented as a Web application. Medical alert application 210 may be configured to accept hypertext transport protocol (HTTP) requests from client devices such those associated with medical personnel alert system 104, patient monitor system 106, and/or data generation system 108 and to send HTTP responses along with optional additional data content which may include web pages such as hypertext markup language (HTML) documents and linked objects in response to the HTTP requests.

Medical alert application 210 further may provide information or data organized in the form of a website accessible over network 110. A website may comprise multiple web pages that display a specific set of information and may contain hyperlinks to other web pages with related or additional information. Each web page is identified by a uniform resource locator (URL) that includes the location or address of the computing device that contains the resource to be accessed in addition to the location of the resource on that computing device. The type of file or resource depends on the Internet application protocol. For example, HTTP and HTTP secure (HTTPS) describe a web page to be accessed with a browser application. The file accessed may be a simple text file, an image file, an audio file, a video file, an executable, a common gateway interface application, a Java applet, or any other type of file supported by HTTP.

Figure 3:
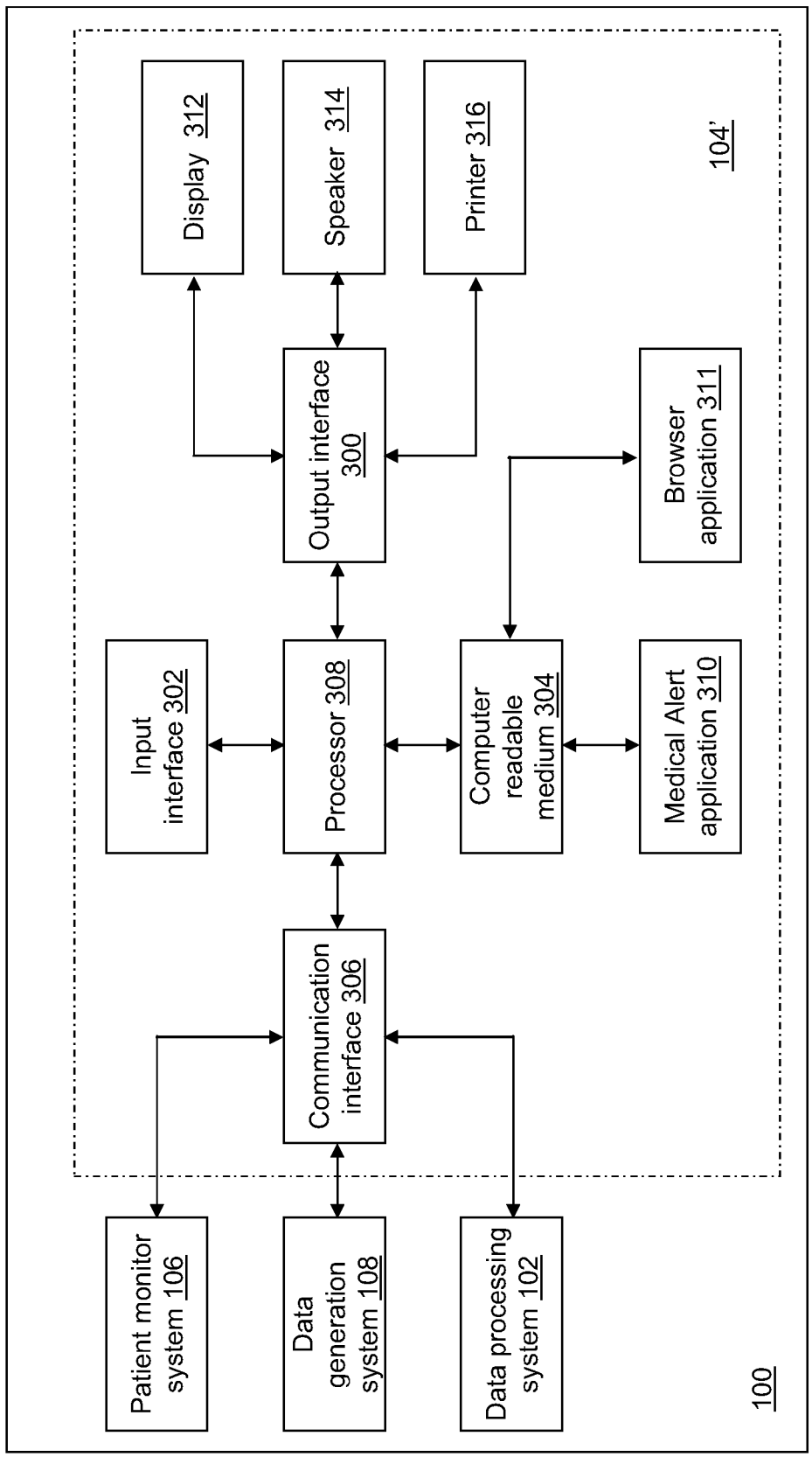
FIG. 3 depicts a block diagram of a medical personnel alert device of the medical alert system of FIG. 1 in accordance with an example embodiment.

With reference to FIG. 3, a block diagram of medical personnel alert device 104' is shown in accordance with an example embodiment. Medical personnel alert device 104' is an example computing device of medical personnel alert system 104. Medical personnel alert device 104' may include a second output interface 300, a second input interface 302, a second computer-readable medium 304, a second communication interface 306, a second processor 308, a second medical alert application 310, a browser application 311, a second display 312, a second speaker 314, and a second printer 316. Different and additional components may be incorporated into medical personnel alert device 104'.

Second output interface 300 provides the same or similar functionality as that described with reference to output interface 200 of server computing device 112. Second input interface 302 provides the same or similar functionality as that described with reference to input interface 202 of server computing device 112. Second computer-readable medium 304 provides the same or similar functionality as that described with reference to computer-readable medium 204 of server computing device 112. Second communication interface 306 provides the same or similar functionality as that described with reference to communication interface 206 of server computing device 112. Second processor 308 provides the same or similar functionality as that described with reference to processor 208 of server computing device 112. Second medical alert application 310 and medical alert application 210 may be the same or different applications or part of an integrated, distributed application. Second display 312 provides the same or similar functionality as that described with reference to display 212 of server computing device 112. Second speaker 314 provides the same or similar functionality as that described with reference to speaker 214 of server computing device 112. Second printer 316 provides the same or similar functionality as that described with reference to printer 216 of server computing device 112.

Browser application 311 performs operations associated with retrieving, presenting, and traversing information resources provided by a web application and/or web server as known to those skilled in the art. An information resource is identified by a uniform resource identifier (URI) and may be a web page, image, video, or other piece of content. Hyperlinks in resources enable users to navigate to related resources. Example browser applications 311 include Navigator by Netscape Communications Corporation, Firefox® by Mozilla Corporation, Opera by Opera Software Corporation, Internet Explorer® by Microsoft Corporation, Safari by Apple Inc., Chrome by Google Inc., etc. as known to those skilled in the art.

Figure 4:
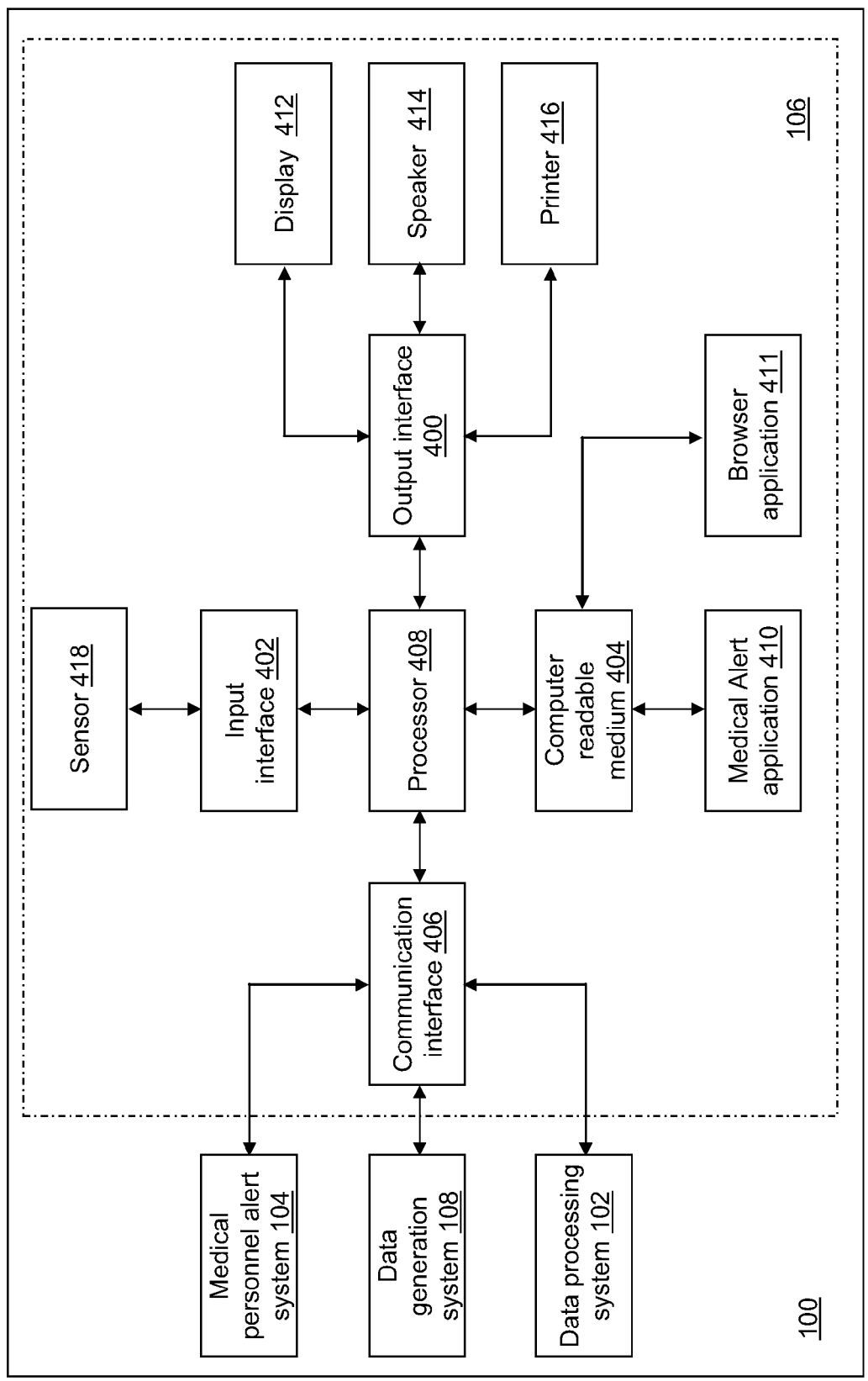
FIG. 4 depicts a block diagram of a patient monitor system of the medical alert system of FIG. 1 in accordance with an example embodiment.

With reference to FIG. 4, a block diagram of patient monitor system 106 is shown in accordance with an example embodiment. Patient monitor system 106 may include a third output interface 400, a third input interface 402, a third computer-readable medium 404, a third communication interface 406, a third processor 408, a third medical alert application 410, a second browser application 411, a third display 412, a third speaker 414, a third printer 416, and a sensor 418. Different and additional components may be incorporated into patient monitor system 106.

Third output interface 400 provides the same or similar functionality as that described with reference to output interface 200 of server computing device 112. Third input interface 402 provides the same or similar functionality as that described with reference to input interface 202 of server computing device 112. Third computer-readable medium 404 provides the same or similar functionality as that described with reference to computer-readable medium 204 of server computing device 112. Third communication interface 406 provides the same or similar functionality as that described with reference to communication interface 206 of server computing device 112. Third processor 408 provides the same or similar functionality as that described with reference to processor 208 of server computing device 112. Third medical alert application 410, second medical alert application 310, and/or medical alert application 210 may be the same or different applications or part of an integrated, distributed application. Second browser application 411 and browser application 311 may be the same or different applications. Third display 412 provides the same or similar functionality as that described with reference to display 212 of server computing device 112. Third speaker 414 provides the same or similar functionality as that described with reference to speaker 214 of server computing device 112. Third printer 416 provides the same or similar functionality as that described with reference to printer 216 of server computing device 112.

Sensor 418 monitors, senses, measures, and/or detects, one or more physiological characteristics of a patient such as heart rate, respiratory rate, cardiac rhythm, blood pressure, oxygen saturation, blood chemistry, etc. Patient monitor system 106 may include a plurality of sensors that use the same or a different sensing/detection technology. Sensor 418 provides the data through input interface 402 to patient monitor system 106 which may provide the data through communication interface 406 to one or more of medical personnel alert system 104, data generation system 108, and data processing system 102.

Figure 5:
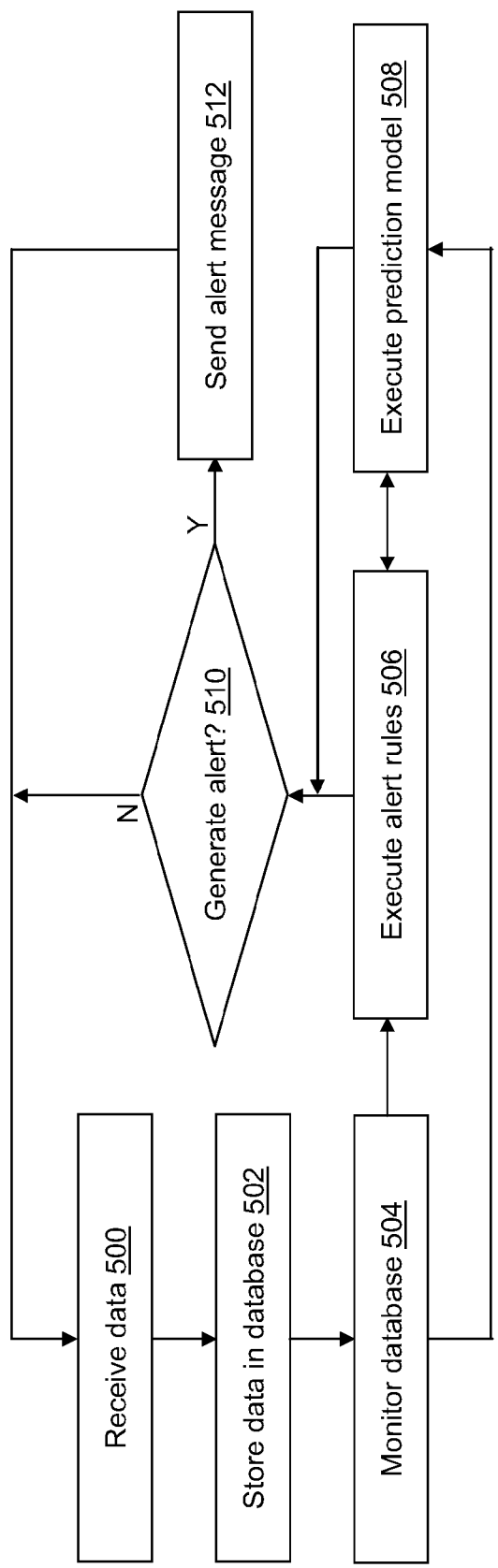
FIG. 5 depicts a flow diagram illustrating example operations performed using medical alert application of the server computing device of FIG. 2, the medical personnel alert device of FIG. 3, and/or the patient monitor system of FIG. 4 in accordance with an example embodiment.

With reference to FIG. 5, example operations associated with medical alert application 210, second medical alert application 310, and/or third medical alert application 410 are described. Additional, fewer, or different operations may be performed depending on the embodiment. The order of presentation of the operations of FIG. 5 is not intended to be limiting. In addition, although some of the operational flows are presented in sequence, the various operations may be performed in various repetitions, concurrently, and/or in other orders than those that are illustrated. In an operation 500, data associated with a physiological characteristic of a patient is received. The data may be received from one or more of medical personnel alert system 104, data generation system 108, data processing system 102, and patient monitor system 106. In an operation 502, the received data is stored, for example, in a table of database 114. In an example embodiment, the tables are enabled with Oracle® Total Recall and automatically keep a history of changes for each record. Using Oracle® Total Recall, each sensor and/or data source can be represented by a single record in database 114 and each time the state or the value changes, the record is updated. Thus, a normal "SELECT" on the table retrieves the most recent value of each sensor while a "SELECT" using the "AS OF" or "VERSIONS" clauses supported by Oracle® Total Recall retrieves the history of past states.

In an operation 504, the data in database 114 is monitored. In an example embodiment, Oracle® Continuous Query Notification monitors changes to a data state, generates corresponding event objects, and sends them to be consumed by Oracle® Rules Manager by calling its "add_event function".

In an operation 506, an alert rule is executed. In an example embodiment, the alert rule is stored in a table of database 114. The alert rule may be a simple alert rule or a complex alert rule. In an example embodiment, Oracle® Rules Manager evaluates the alert rule or rules and triggers actions to alert medical personnel such as doctors and nurses about a condition of a patient through a dashboard presented under control of medical alert application 210, second medical alert application 310, and/or third medical alert application 410 possibly using mobile device communication channels. Some alert rules may also trigger calls to data mining models to apply predictions in real time by executing a prediction model as indicated in an operation 508. The results may be sent back to the Oracle® Rules Manager executing an alert rule, which evaluates new alert rules to determine if those results should be sent to medical personnel as well. As a result, the prediction model execution may not be applied each time the data changes. As described later, the alert rules are highly customizable such that medical personnel can create, edit, and delete rules and/or override other existing rules.

In an operation 510, a determination is made concerning whether or not an alert is generated based on the alert rule execution and/or prediction model execution. If a determination is made that an alert should not be generated, processing continues at operation 500. If a determination is made that an alert should be generated, in an operation 512, an alert is generated and processing continues at operation 500. For example, an alert may be sent to one or more medical personnel alert device 104' of medical personnel such as doctors and nurses. The alert may be in the form of a dashboard presented under control of second medical alert application 310 and/or browser application 311 executing at medical personnel alert device 104'.

Figure 6:
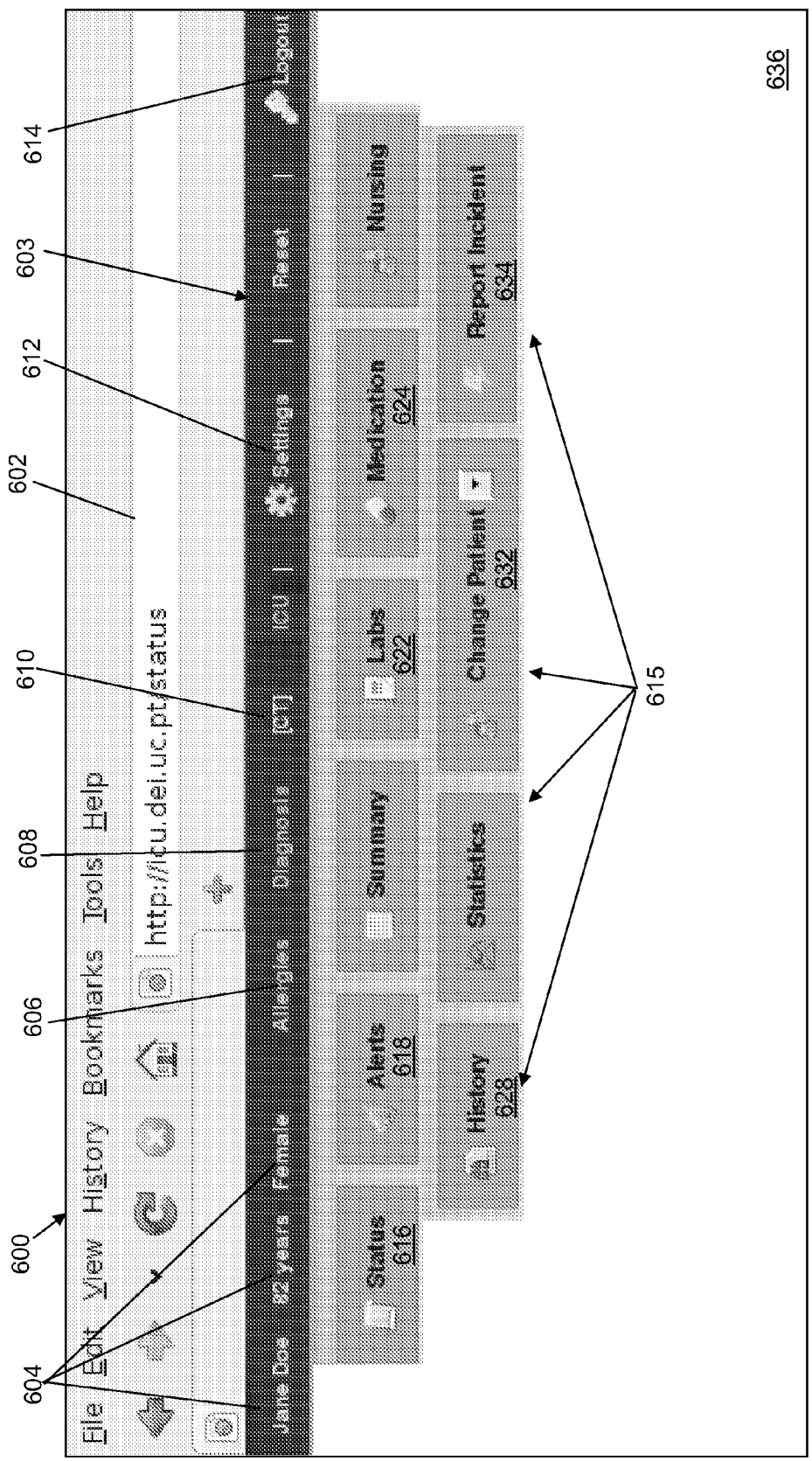

For example, with reference to FIG. 6, browser application 311 in combination with second medical alert application 310 installed at medical personnel alert device 104' receives the alert from medical alert application 210 hosted at server computing device 112. Through interaction with medical alert application 210, browser application 311 in combination with second medical alert application 310 controls presentation of a first user interface window 600 at medical personnel alert device 104'. Second browser application 411 in combination with third medical alert application 410 and medical alert application 210 may provide the same or similar functionality at patient monitor system 106 as that described at medical personnel alert device 104'.

First user interface window 600 may include a plurality of menus and buttons associated with browser application 311 including a URL window 602 into which a URL associated with medical alert application 210 hosted at server computing device 112 may be entered as known to those skilled in the art. First user interface window 600 also may include an information summary toolbar 603 which may include patient demographic information 604, an allergies button 606, a diagnosis button 608, a protocol indicator 610, a settings button 612, and a logout button 614. Patient demographic information 604 may include a patient name, age, and sex. A variety of different types of user interface controls may be included in first user interface window 600 without limitation such as buttons, drop down menus, tabs, shortcut keys, toolbars, radio buttons, checkboxes, etc. as known to a person of skill in the art. Those shown herein are merely representative of the controls which can be used to provide the described functionality.

Upon receipt of an indication of a user selection of allergies button 606, a list of allergies of the patient indicated in patient demographic information 604 is presented to the user in display 312 and/or display 412. Upon receipt of an indication of a user selection of diagnosis button 608, a summary of the diagnosis for the patient indicated in patient demographic information 604 is presented to the user in display 312 and/or display 412. Protocol indicator 610 indicates the protocol for which the patient indicated in patient demographic information 604 was admitted. For example, in the example of FIG. 6, the patient "Jane Doe" is admitted as a cardiothoracic (CT) patient to the intensive care unit (ICU).

Figure 7:
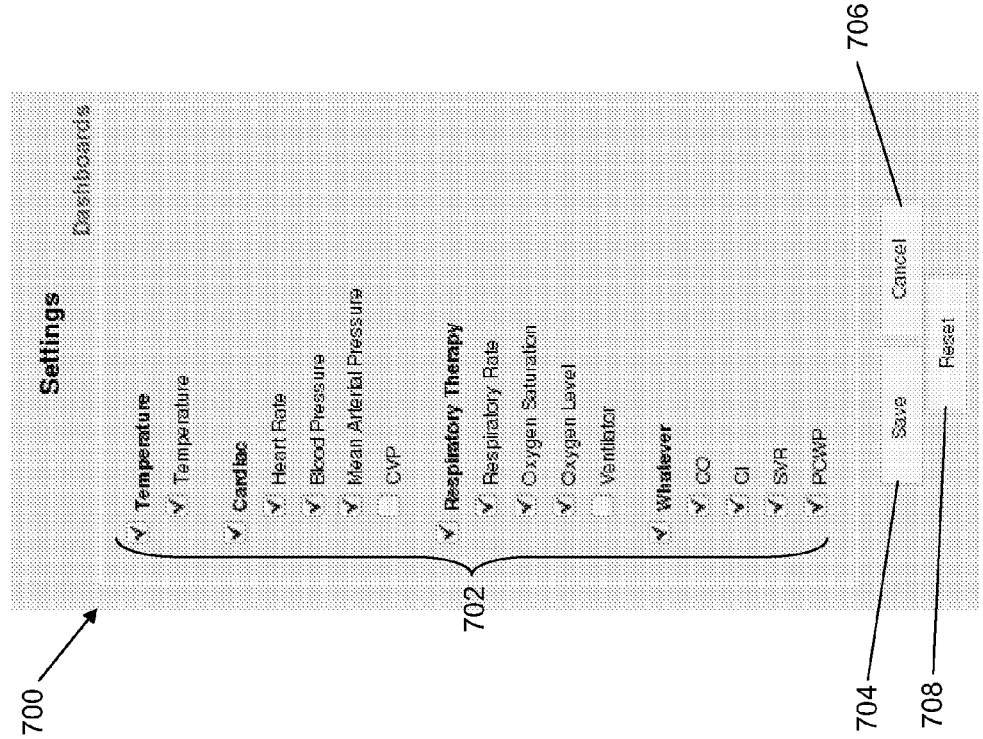

Upon receipt of an indication of a user selection of settings button 612, a list of physiological characteristics to be displayed in a dashboard space 636 for the patient indicated in patient demographic information 604 is presented to the user in display 312 and/or display 412. For example, with reference to FIG. 7, a second user interface window 700 is presented under control of browser application 311 in combination with second medical alert application 310 and through interaction with medical alert application 210 at medical personnel alert device 104'. Second user interface window 700 may include a plurality of checkboxes 702 each associated with a physiological characteristic and possibly organized by type. For example, second user interface window 700 may include physiological characteristics such as temperature, heart rate, blood pressure, mean arterial pressure, central venous pressure (CVP), respiratory rate, oxygen saturation, oxygen level, ventilator use, cardiac output (CO), cardiac index (CI), systemic vascular resistance (SVR), pulmonary capillary wedge pressure (PCWP), etc.

Second user interface window 700 further may include a save button 704, a cancel button 706, and a reset button 708. Upon receipt of an indication of a user selection of save button 704, the selected physiological characteristics are saved for the patient indicated in patient demographic information 604, second user interface window 700 is closed, and the selected physiological characteristics are presented in dashboard space 636 shown with reference to FIG. 6. Upon receipt of an indication of a user selection of cancel button 706, the selected physiological characteristics are ignored and second user interface window 700 is closed. Upon receipt of an indication of a user selection of reset button 708, the selected physiological characteristics are reset to a set of default characteristics for the patient indicated in patient demographic information 604, second user interface window 700 is closed, and the default physiological characteristics are presented in dashboard space 636 shown with reference to FIG. 6. In an example embodiment, the default physiological characteristics are selected based on the protocol for which the patient is admitted.

With continuing reference to FIG. 6, upon receipt of an indication of a user selection of logout button 614, a confirmation window may be presented to the user to request confirmation that the user is requesting to logout from third medical alert application 410, second medical alert application 310, and/or medical alert application 210. As known to those skilled in the art, the user may have logged into third medical alert application 410, second medical alert application 310, and/or medical alert application 210 using a username and password when initially requesting access to the URL entered in URL window 602. The username may be associated with an account that is associated with a medical personnel group such as nurse, medical technician, physician, etc. and/or a specific individual. Thus, the information saved through interaction with third medical alert application 410, second medical alert application 310, and/or medical alert application 210 may be associated with the user so that the information presented is customized for the user including the generation of alerts as will be discussed further below.

First user interface window 600 also may include a plurality of action buttons 615. The plurality of action buttons 615 may include a status button 616, an alert button 618, a summary button, a labs button 622, a medication button 624, a nursing button, a history button 628, a statistics button, a change patient button 632, and a report incident button 634. A fewer or a greater number and type of buttons may be included without limitation. Upon receipt of an indication of a user selection of a button of the plurality of action buttons 615, information may be presented to the user in dashboard space 636 for the patient indicated in patient demographic information 604.

Upon receipt of an indication of a user selection of status button 616, one or more indicators associated with the physiological characteristics selected using second user interface window 700 are displayed in dashboard space 636 for the patient indicated in patient demographic information 604. For example, with reference to FIG. 8, dashboard space 636 includes a plurality of physiological characteristic indicator boxes 800 presented under control of browser application 311 in combination with second medical alert application 310 and through interaction with medical alert application 210 at medical personnel alert device 104'.

Figure 8:
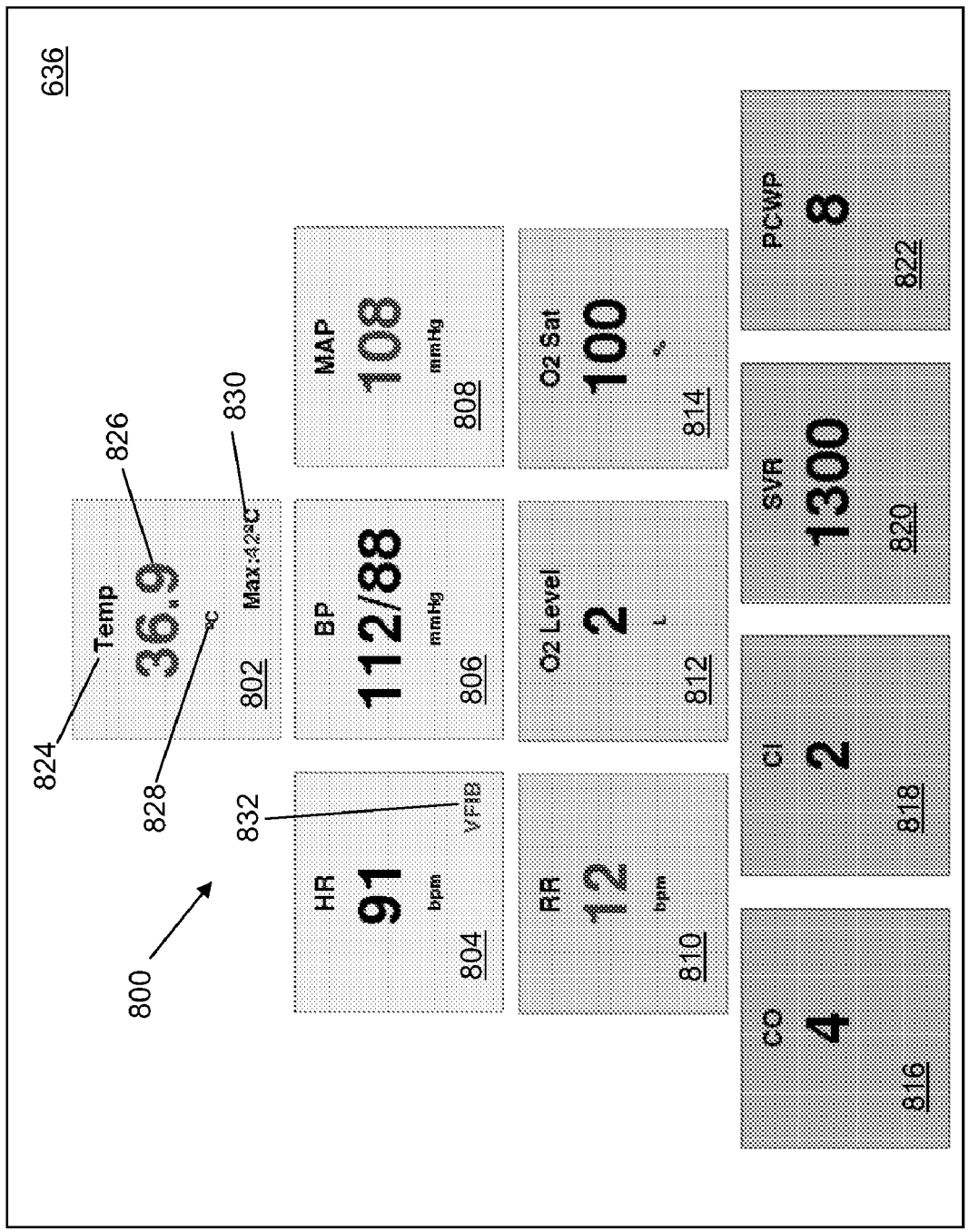

The example shown with reference to FIG. 8 includes a temperature (Temp) indicator box 802, a heart rate (HR) indicator box 804, a blood pressure (BP) indicator box 806, a mean arterial pressure (MAP) indicator box 808, a respiratory rate (RR) indicator box 810, an oxygen level (O2 Level) indicator box 812, an oxygen saturation (O2 Sat) indicator box 814, a CO indicator box 816, a CI indicator box 818, an SVR indicator box 820, and a PCWP indicator box 822. Each physiological characteristic indicator box includes an indicator of the physiological characteristic such as "Temp" for temperature, "HR" for heart rate, "BP" for blood pressure, etc. and a most recently measured value of the physiological characteristic possibly measured using patient monitor system 106. For example, a temperature indicator box 802 includes an indicator 824 and a measured value 826.

A physiological characteristic indicator box also may include a units indicator associated with the measured value and additional information associated with the measured value. For example, temperature indicator box 802 further may include a units indicator 828 indicating "° C." and a maximum temperature indicator 830 determined over a previous time window such as the last hour, the last 12 hours, etc. Heart rate indicator box 804 may include an indicator 832 that the patient is in ventricular fibrillation by indicating "VFIB" in a portion of heart rate indicator box 804. Additionally, the physiological characteristic indicator boxes may be grouped on different rows and shown using different colors or shading to differentiate the boxes associated with different types of measurements such as cardiac measurements, respiratory therapy measurements, etc. Further, some or all of the information in each physiological characteristic indicator box may be colorized to indicate whether or not a measured value is of concern. For example, if the most recently measured value for the physiological characteristic is "normal" for the patient, the color used may be black; whereas other colors such as yellow, orange, and/or red may be used to indicate a successively more serious abnormal measured value.

Figure 9:
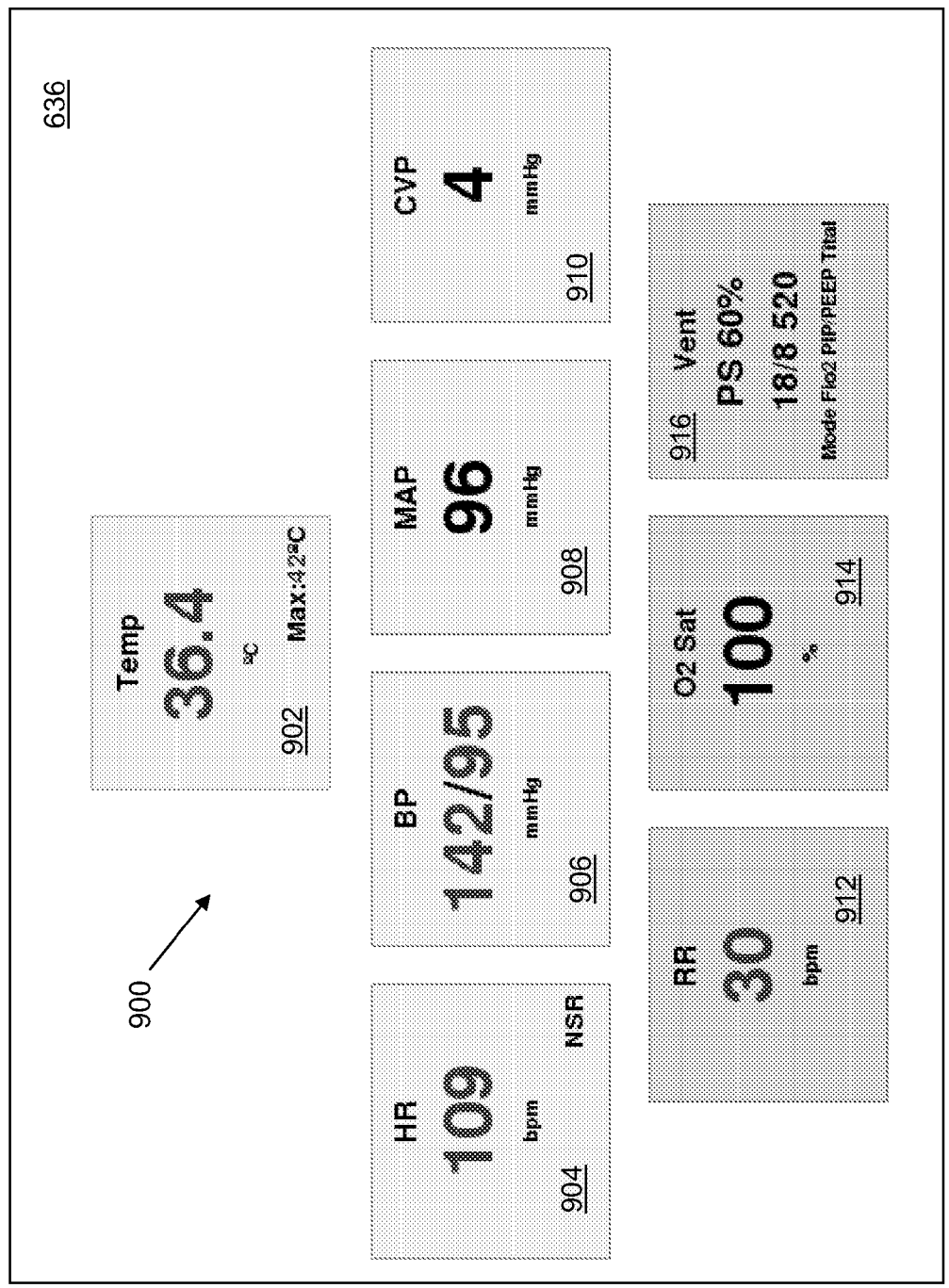

As another example, with reference to FIG. 9, dashboard space 636 includes a second plurality of physiological characteristic indicator boxes 900 presented under control of browser application 311 in combination with second medical alert application 310 and through interaction with medical alert application 210 at medical personnel alert device 104'. The example shown with reference to FIG. 9 includes a temperature indicator box 902, an HR indicator box 904, a BP indicator box 906, a MAP indicator box 908, a CVP indicator box 910, an RR indicator box 912, an O2 Sat indicator box 914, and a ventilator (Vent) indicator box 916 selected for presentation possibly for a different patient admitted for a different condition.

Figure 10:
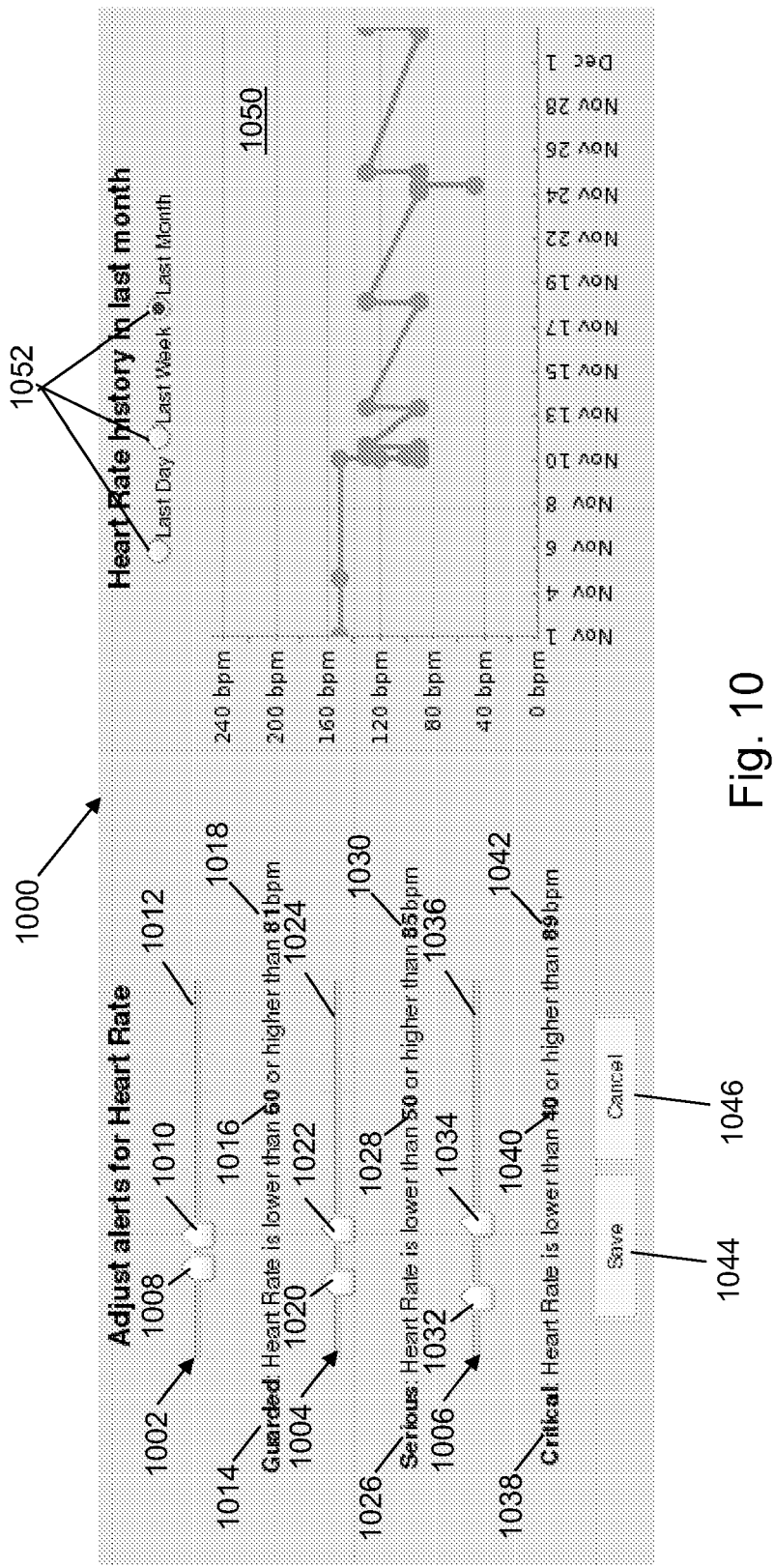

Upon receipt of an indication of a user selection of a physiological characteristic indicator box, a third user interface window 1000 may be presented under control of browser application 311 in combination with second medical alert application 310 and through interaction with medical alert application 210 at medical personnel alert device 104' in accordance with an example embodiment as shown with reference to FIG. 10. Third user interface window 1000 may include one or more alert rule related to the selected physiological characteristic. For example, with reference to FIG. 10, third user interface window 1000 includes a first alert range 1002, a second alert range 1004, and a third alert range 1006 associated with a heart rate, each of which constitutes a simple alert rule. First alert range 1002 is indicated using a first arrow 1008 for a minimum value and a second arrow 1010 for a maximum value on a slider bar 1012. To adjust first alert range 1002, the user may drag first arrow 1008 and/or second arrow 1010 along slider bar 1012. Range information text 1014 indicates the condition priority level associated with first alert range 1002. For example, range information text 1014 may indicate that a "Guarded" condition level is associated with first alert range 1002. Range information text 1014 further may indicate a first numerical value 1016 indicated by the location of first arrow 1008 and a second numerical value 1018 indicated by the location of second arrow 1010.

Second alert range 1004 may be similarly indicated using a first arrow 1020 for a minimum value and a second arrow 1022 for a maximum value on a slider bar 1024. To adjust second alert range 1004, the user may drag first arrow 1020 and/or second arrow 1022 along slider bar 1024. Range information text 1026 indicates the condition priority level associated with second alert range 1004. For example, range information text 1026 may indicate that a "Serious" condition level is associated with second alert range 1004. Range information text 1026 further may indicate a first numerical value 1028 indicated by the location of first arrow 1020 and a second numerical value 1030 indicated by the location of second arrow 1022.

Third alert range 1006 may be similarly indicated using a first arrow 1032 for a minimum value and a second arrow 1034 for a maximum value on a slider bar 1036. To adjust third alert range 1006, the user may drag first arrow 1032 and/or second arrow 1034 along slider bar 1036. Range information text 1038 indicates the condition priority level associated with third alert range 1006. For example, range information text 1038 may indicate that a "Critical" condition level is associated with third alert range 1006. Range information text 1038 further may indicate a first numerical value 1040 indicated by the location of first arrow 1032 and a second numerical value 1042 indicated by the location of second arrow 1034.

Movement of first arrow 1008 and/or second arrow 1010 of first alert range 1002 may automatically cause movement of first arrow 1020 and/or second arrow 1022 of second alert range 1004 and of first arrow 1032 and/or second arrow 1034 of third alert range 1006 so that first numerical value 1016 and/or second numerical value 1018 of first alert range 1002 are within the values indicated by first arrow 1020 and/or second arrow 1022 of second alert range 1004 and by first arrow 1032 and/or second arrow 1034 of third alert range 1006. Additionally, movement of first arrow 1020 and/or second arrow 1022 of second alert range 1004 may automatically cause movement of first arrow 1032 and/or second arrow 1034 of third alert range 1006 so that first numerical value 1028 and/or second numerical value 1030 of second alert range 1004 are within the values indicated by first arrow 1032 and/or second arrow 1034 of third alert range 1006.

Third user interface window 1000 further may include a save button 1044 and a cancel button 1046. Upon receipt of an indication of a user selection of save button 1044, the adjusted alert range values are saved for the patient indicated in patient demographic information 604 and third user interface window 1000 is closed. In an example embodiment, the adjusted alert range values are also associated with the user adjusting the values based on the account associated with the username and password. Thus, the adjusted alert range values may be customized for the patient and/or medical personnel adjusting the alert values. Of course, not all medical personnel may have permission to adjust the alert values. Upon receipt of an indication of a user selection of cancel button 1046, the adjusted alert range values are ignored and third user interface window 1000 is closed.

Third user interface window 1000 further may include a history graph 1050 associated with the selected physiological characteristic. For example, history graph 1050 may include a plot of the values of the heart rate of the patient over a user selectable time period. The time period may be selected using radio buttons 1052 which may be associated with a plurality of different time periods. For example, the time periods may be within the last day, the last week, the last month, etc.

With reference to FIG. 11, an alert rule table 1100 summarizes a series of alert rule range values for various physiological characteristics in accordance with an example embodiment. Alert rules may be predefined for a general patient population based on the values indicated in alert rule table 1100. Alternatively, a different table of alert values may be defined based on the protocol for which the patient is admitted, based on a group of medical personnel such as a nurse or a physician, based on a specific medical person such as a specific physician, based on a specific type of physician such as a surgeon or a cardiothoracic specialist, etc. Depending on the physiological characteristic, the alert value may not comprise a range defined by a maximum value and a minimum value. For example, an intra-abdominal pressure alert rule may include only alert values associated with a maximum value. Additionally, a different number of condition priority levels may be used depending on the physiological characteristic. For example, an cardiac output level alert rule may include only "Guarded" and "Critical" alert ranges.

Figure 12:
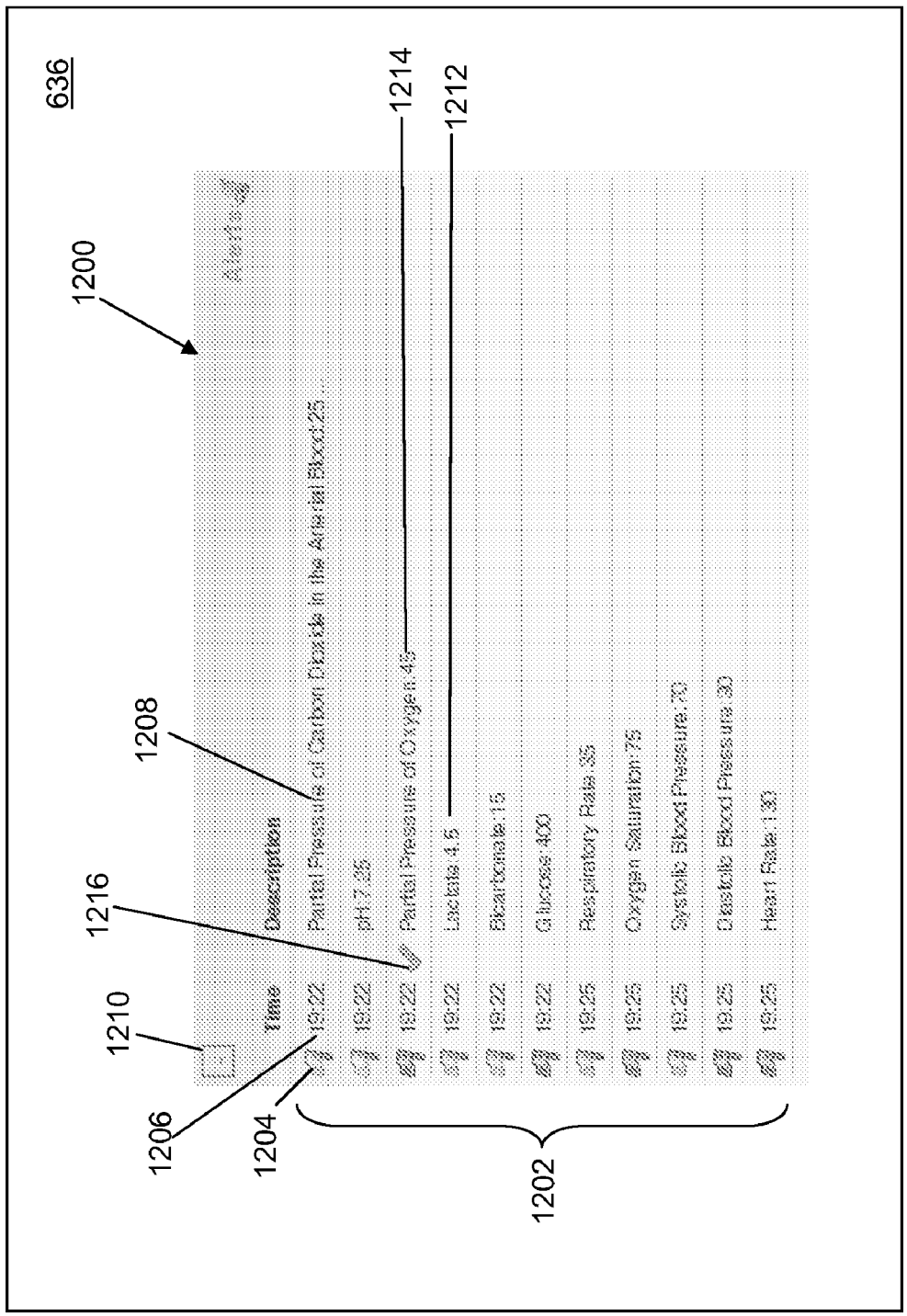

Upon receipt of the indication of the user selection of status button 616, dashboard space 636 may further include an alert status for the patient indicated in patient demographic information 604. For example, with reference to FIG. 12, dashboard space 636 may further include an alert status window 1200 presented under control of browser application 311 in combination with second medical alert application 310 and through interaction with medical alert application 210 at medical personnel alert device 104'. Alert status window 1200 may include one or more alerts 1202 generated based on execution of an alert rule triggered based on receipt of a measured value of a physiological characteristic. For example, patient monitor system 106 may measure a blood pressure of a patient which is sent to data processing system 102 and stored in database 114 for comparison with an alert rule or rules associated with the blood pressure. Thus, the measured value of the physiological characteristic is sent by patient monitor system 106 and received by data processing system 102 along with a characteristic indicator of the physiological characteristic which indicates to which physiological characteristic the measured value is associated. An applicable alert rule may be identified by comparing the characteristic indicator of the measured value to the physiological characteristic indicator associated with the alert rule. An application type indicator for the alert rule indicating a group for which to apply the alert rule also may be associated with the alert rule. For example, the alert rule may apply to all patients, only to those patients admitted under a specific protocol, only to a specific patient, only to those patients of a specific physician, only to a specific patient for a specific physician, etc. Thus, the application type indicator indicates to which groups the alert rule is applied. The group indicators associated with the measured value such as the patient name or other indicator such as an admission number, the physician, the protocol for which the patient is admitted, etc. also may be compared to the application type indicator for the alert rule to determine if the alert rule is applied. If the alert rule is applied and the received, measured value of the physiological characteristic satisfies the alert rule, the alert is generated and listed in alert status window 1200.

The one or more alerts 1202 include an urgency indicator 1204, a time value 1206, and a description 1208. Urgency indicator 1204 indicates an urgency or seriousness of the patient's condition based on the measured physiological characteristic. For example, a first urgency indicator may indicate a "Guarded" condition level, a second urgency indicator may indicate a "Serious" condition level, and a third urgency indicator may indicate a "Critical" condition level. The different indications may be provided using different colors such as yellow for the "Guarded" condition level, orange for the "Serious" condition level, and red for the "Critical" condition level. Time value 1206 indicates the approximate time at which the measurement was taken based on which the alert was generated. Description 1208 provides an explanation as to why the alert was generated.

Alert status window 1200 also may include a collapse button 1210. Upon receipt of an indication of a user selection of collapse button 1210, alert status window 1200 may be collapsed to reduce the amount of space occupied by alert status window 1200 in dashboard 636. Upon receipt of an indication of a second user selection of collapse button 1210, alert status window 1200 may be expanded to again display the entire alert status window 1200 in dashboard 636.

Upon receipt of an indication of a user selection of an alert of the one or more alerts 1202, a detailed description of the alert may be presented. For example, with reference to FIG. 13, an alert description window 1300 may be presented under control of browser application 311 in combination with second medical alert application 310 and through interaction with medical alert application 210 at medical personnel alert device 104' after receipt of an indication of a user selection of a lactate alert 1212 shown with reference to FIG. 12. As known to a person of skill in the art, lactate alert 1212 may be selected by double-clicking on, for example, urgency indicator 1204, time value 1206, and/or description 1208 associated with lactate alert 1212.

Alert description window 1300 may include a condition priority value 1302, an alert rule identifier 1304, an alert description 1306, an alert content 1308, an alert proposed action 1310, an alert time and date 1312, a resolution indicator 1314, a solve button 1316, and an OK button 1318. Condition priority value 1302 may be associated with the urgency indicator 1204. For example, condition priority value 1302 may indicate whether the generated alert is associated with a "Guarded" condition level, a "Serious" condition level, or a "Critical" condition level. Alert rule identifier 1304 indicates an alert rule used to generate the alert and may be associated with a table identifier value associated with the alert rule. Alert description 1306 includes a first text field describing the alert. Alert content 1308 includes a second text field summarizing the alert. In an example embodiment, the second text field corresponds to description 1208 associated with lactate alert 1212. Alert proposed action 1310 includes a third text field proposing a response to the alert or a possible cause of the alert generation. Alert time and date 1312 indicates the time that the alert was generated.

Resolution indicator 1314 indicates whether or not an action has been taken to resolve the alert. Upon receipt of an indication of a user selection of solve button 1316, a text box window is opened to allow the user to enter an explanation of the action taken to resolve the alert. Upon receipt of an indication of a user closing the text box window, the explanation of the action taken to resolve the alert may be shown in resolution indicator 1314 and solve button 1316 may be removed from alert description window 1300. For example, with reference to FIG. 14, a second alert description window 1400 may be presented under control of browser application 311 in combination with second medical alert application 310 and through interaction with medical alert application 210 at medical personnel alert device 104' after receipt of an indication of a user selection of an oxygen alert 1214 shown with reference to FIG. 12. Resolution indicator 1314 includes the explanation of the action taken to resolve the alert as entered by the user in the text box window. Upon receipt of an indication of a user selection of OK button 1318, second alert description window 1400 is closed. Additionally, with reference to FIG. 12, oxygen alert 1214 may include a resolution indicator 1216 indicating that the alert has been resolved.

Upon receipt of an indication of a user selection of alert button 618, dashboard space 636 may include an alert rule list. For example, with reference to FIG. 15, dashboard space 636 may include an alert rule list 1500 presented under control of browser application 311 in combination with second medical alert application 310 and through interaction with medical alert application 210 at medical personnel alert device 104'. Alert rule list 1500 may include one or more alert rules 1502. In an example embodiment, different alert rule lists may be associated with different conditions. For example, alert rule list 1500 may be associated with a "General" tab 1504. Selection of a "Cardiac Arrest" tab 1506 may cause presentation of alert rules associated with a patient admitted for a cardiac arrest; whereas, selection of a "Respiratory Failure" tab 1508 may cause presentation of alert rules associated with a patient admitted for respiratory failure. Alert rule list 1500 may not be conveniently displayed in a single page. As a result, a page selector 1510 allows the user to select successive pages containing additional alert rules in alert rule list 1500.

Selection of a "Ranges" tab 1509 may cause presentation of a summary list of alert rules. For example, upon receipt of an indication of a user selection of "Ranges" tab 1509, dashboard space 636 may include a second alert rule list 1600 presented under control of browser application 311 in combination with second medical alert application 310 and through interaction with medical alert application 210 at medical personnel alert device 104'. Second alert rule list 1600 may not be conveniently displayed in a single page. As a result, a second page selector 1604 allows the user to select successive pages containing additional alert rules in second alert rule list 1600.

Second alert rule list 1600 may include one or more summary alert rules 1602. In an example embodiment, each row of alert rule table 1100, shown with reference to FIG. 11, may be indicated as an alert rule of second alert rule list 1600. Each summary alert rule of the one or more summary alert rules 1602 may include a rule identifier 1606 and a rule condition 1608. Rule identifier 1606 may be a unique identifier assigned to each alert rule when the alert rule is created. Rule identifier 1606 may be in an alphanumeric format that indicates the physiological characteristic and the priority level associated with the alert rule. Rule condition 1608 summarizes the test condition satisfaction of which triggers the generation of the alert. For example, rule condition 1608 includes an indicator 1610 of the physiological characteristic to be compared and the test condition 1612 to which a measured value of the physiological characteristic is compared for a matching physiological characteristic based on indicator 1610. If test condition 1612 is satisfied using the measured value of the physiological characteristic inserted for the "value" indicated in test condition 1612, the alert is generated.

Figure 15:
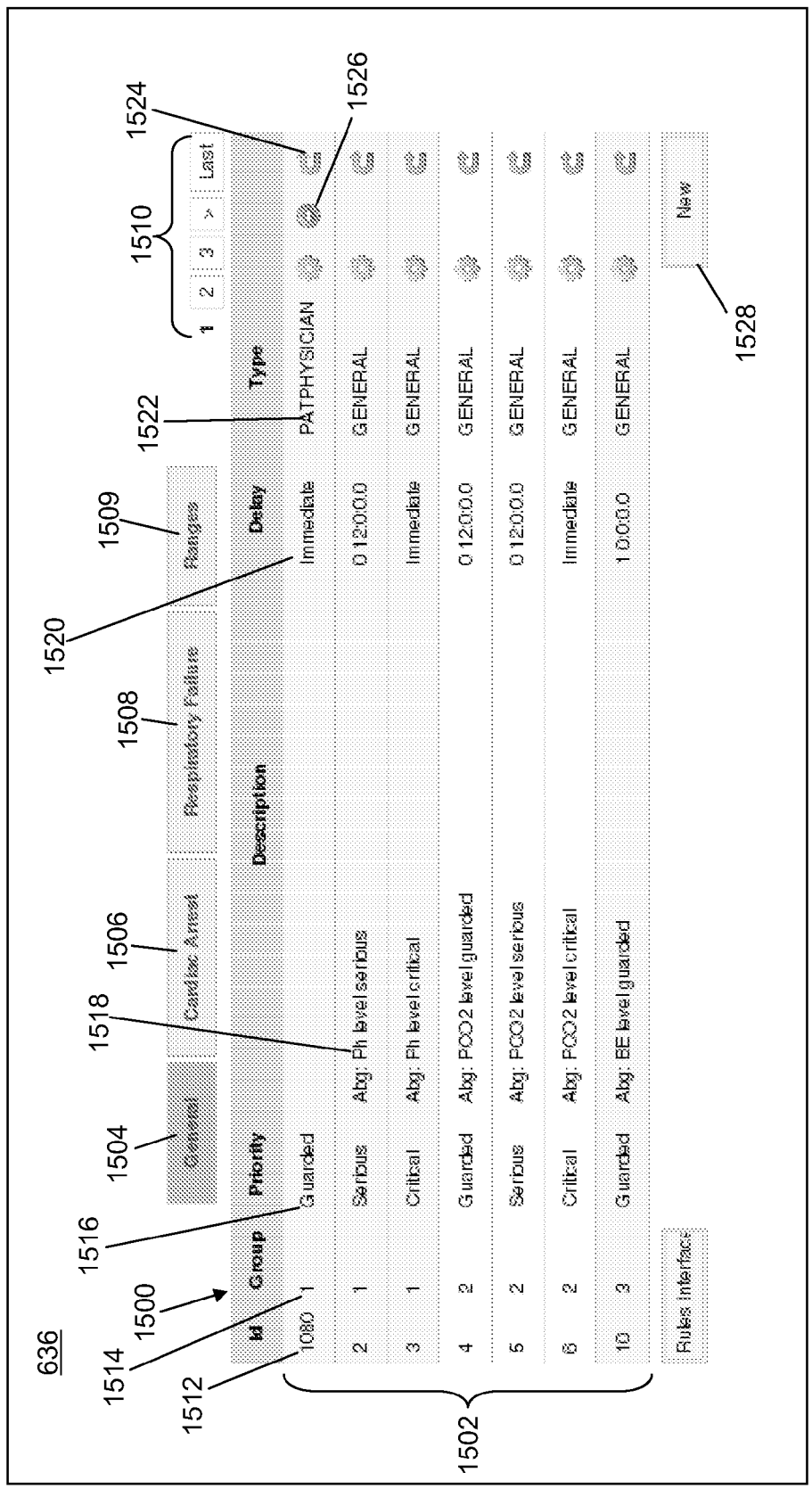
Figure 16:
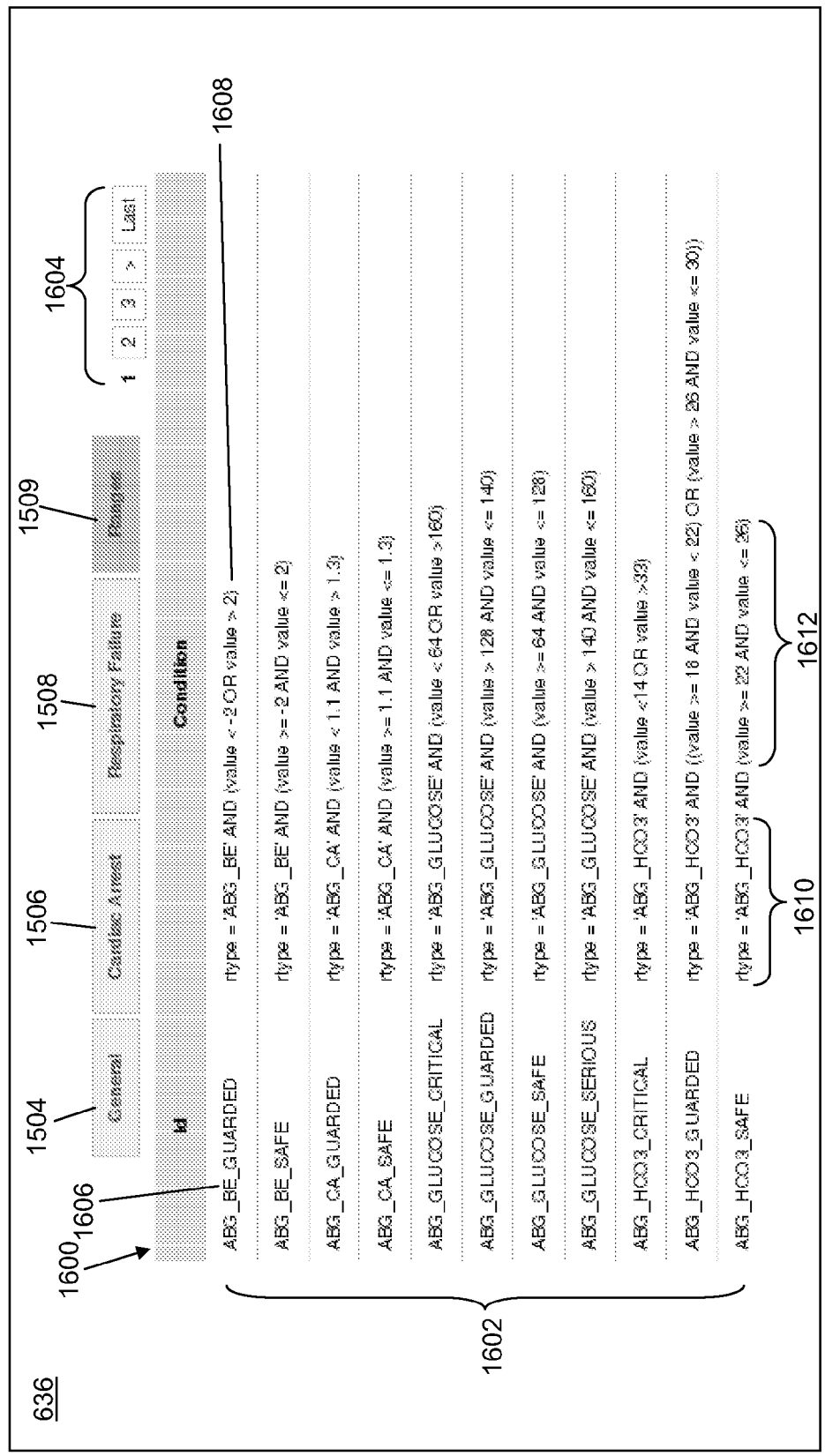

With continuing reference to FIG. 15, each alert rule of alert rule list 1500 may include a rule identifier 1512, a group identifier 1514, a priority level indicator 1516, a description 1518, a delay indicator 1520, an application type indicator 1522, a modifier selector 1524, and an override indicator 1526. Each alert rule of second rule list 1600 may have a corresponding entry in alert rule list 1500. Rule identifier 1512 may be a unique numerical value assigned to each alert rule automatically when the alert rule is created. Rule identifier 1512 may be associated with rule identifier 1606 in an internal table or rule identifier 1512 and rule identifier 1606 may indicate the same value for the same alert rule. Alert rule identifier 1304 shown with reference to FIG. 13 also may be the same value as indicated in rule identifier 1512 for the same alert rule.

Group identifier 1514 may be used to identify a group of alert rules associated with the same physiological characteristic though associated with a different condition priority level and a different test condition. For example, with reference to the example of FIG. 15, the alert rules having rule identifiers "4", "5", and "6" are assigned the same group identifier of "2" because each is associated with the partial pressure of carbon dioxide (PCO2) level though each is associated with a different condition priority level and a different test condition.

Priority level indicator 1516 indicates the condition priority level associated with the alert rule. Description 1518 includes a text field describing the alert and may correspond to the first text field presented in alert description 1306 shown with reference to FIG. 13. Delay indicator 1520 provides an indication of a delay associated with generation of the alert. For example, a time delay value associated with delay indicator 1520 may result in not generating the alert again until expiration of the time delay value after the last alert generation based on the same alert rule. The alert may not be generated unless the condition associated with the comparison is satisfied again after the time delay period.

Application type indicator 1522 indicates to which group the alert rule is applied. Application type indicator 1522 may indicate the alert rule is applied to all patients, a specific patient, all patients of a specific physician, only for a specific patient and physician pair, based on the protocol for which the patient is admitted, etc.

Upon receipt of an indication of a user selection of modifier selector 1524 associated with an alert rule of the one or more alert rules 1502, an alert rule window may be presented under control of browser application 311 in combination with second medical alert application 310 and through interaction with medical alert application 210 at medical personnel alert device 104'. The alert rule window allows the user to adjust the parameters associated with the alert rule. In an example embodiment, the user may only override the alert rule so that the modified alert rule is only associated with the user, and thus, does not effect the alert rules of other users. Override indicator 1526 may be used to indicate that the alert rule is a modified alert rule that is overriding another alert rule.

Selection of a New button 1528 may cause presentation of a plurality of user interface controls that allow the user to define a new alert rule. For example, upon receipt of an indication of a user selection of New button 1528, dashboard space 636 further may include a new rule parameter list 1700 presented under control of browser application 311 in combination with second medical alert application 310 and through interaction with medical alert application 210 at medical personnel alert device 104'. In an alternative embodiment, new rule parameter list 1700 may be presented in a new window. New rule parameter list 1700 may include a group identifier control 1702, a priority level identifier control 1704, an application type indicator control 1706, a time delay control 1708, a description control 1710, an action control 1712, a rule override control 1714, a rule override search control 1716, a rule evaluation control 1718, a time control 1720, a time units selector 1722, a test condition control 1724, a save button 1726, and a cancel button 1728.

Figure 17:
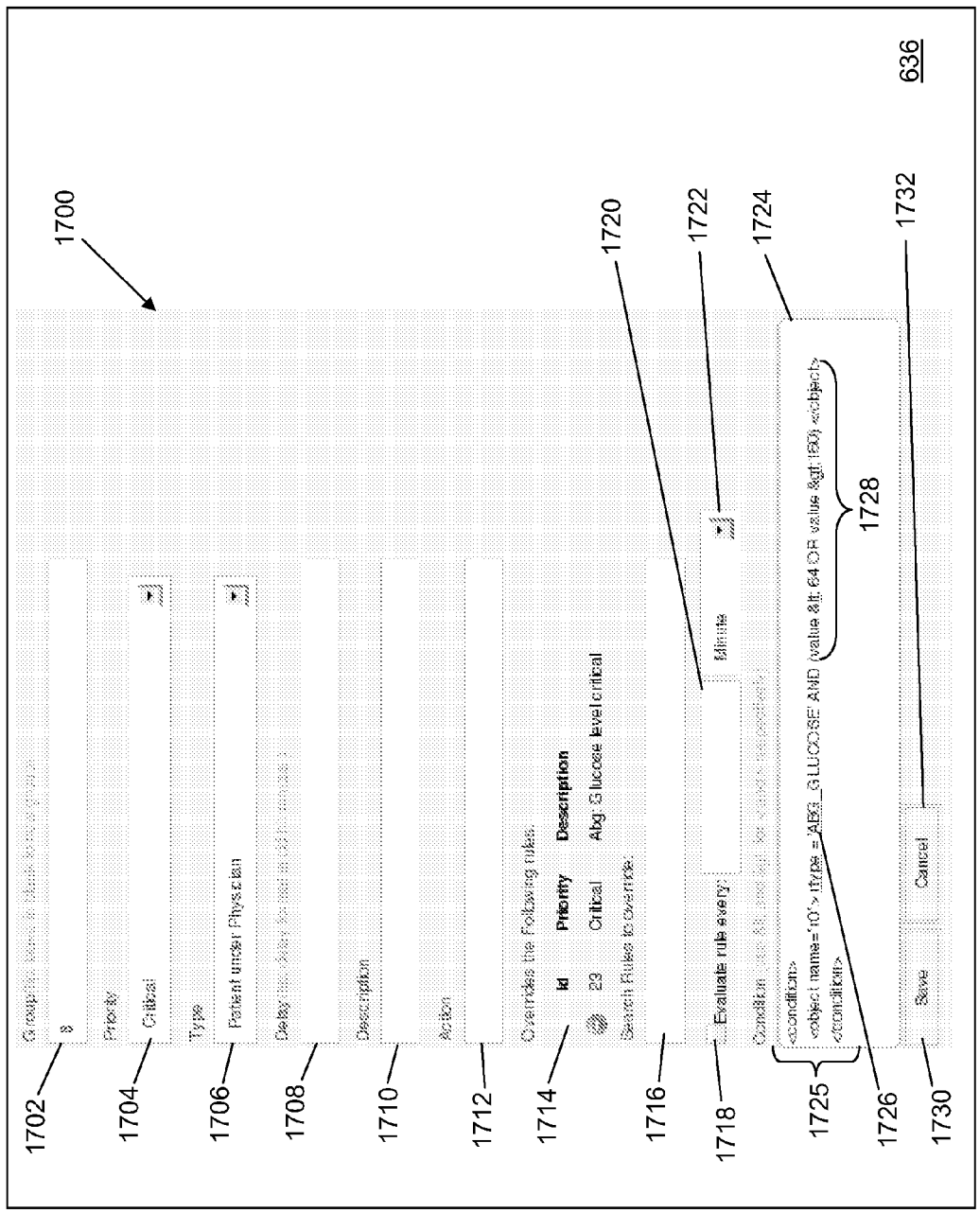

In the example embodiment of FIG. 17, group identifier control 1702 includes a text box user interface control in which the user may enter a group identifier. Group identifier control 1702 may be used to identify a group of alert rules associated with the same physiological characteristic though associated with a different condition priority level and a different test condition. For example, group identifier control 1702 may correspond to group identifier 1514 shown with reference to FIG. 15 after creation of the new alert rule.

In the example embodiment of FIG. 17, priority level identifier control 1704 includes a drop down selector box user interface control from which the user may select a priority level such as "Guarded", "Serious", and "Critical" though other priority levels may be defined. Additionally, a fewer or a greater number of priority levels may be defined for selection by the user. Priority level identifier control 1704 may correspond to priority level indicator 1516 shown with reference to FIG. 15 after creation of the new alert rule.

Figure 18:
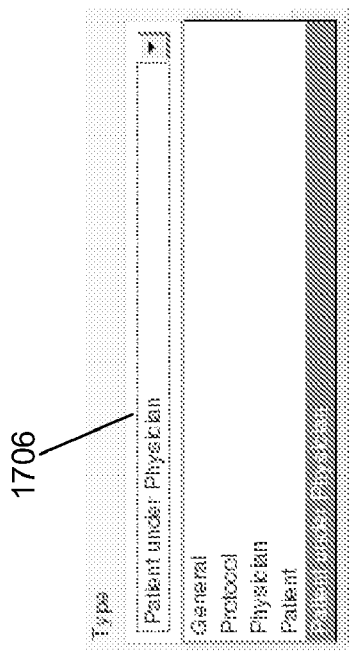

In the example embodiment of FIG. 17, application type indicator control 1706 includes a drop down selector box user interface control from which the user may select an application type. Application type indicator control 1706 indicates to which group the alert rule is applied. For example, with reference to FIG. 18, application types may include "General", "Protocol", "Physician", "Patient", and "Patient under Physician" though other groups may be defined. Selection of the "General" option in the drop down selector box may indicate that the alert rule is applied to all patients. Selection of the "Protocol" option in the drop down selector box may indicate that the alert rule is applied based on the protocol for which the patient is admitted. In an example embodiment, if the "Protocol" option is selected, the protocol may be automatically associated with protocol indicator 610 for the patient indicated in patient demographic information 604. In another example embodiment, if the "Protocol" option is selected, a new drop down selector box may be presented in FIG. 17 or a separate window to allow the user to select the protocol to which the rule is associated. In the new drop down selector box, a default protocol may be automatically indicated based on protocol indicator 610 for the patient indicated in patient demographic information 604. Selection of the "Physician" option in the drop down selector box may indicate that the alert rule is applied to all patients of a specific physician. The specific physician may default to the current user based on the login information or the user may be requested to select a physician from a list of physicians. Selection of the "Patient" option in the drop down selector box may indicate that the alert rule is applied to a specific patient. The specific patient may default to the patient indicated in patient demographic information 604 or the user may be requested to select a patient from a list of patients. Selection of the "Patient under Physician" option in the drop down selector box may indicate that the alert rule is applied to a specific patient and physician pair. Additionally, a fewer or a greater number of application types may be defined for selection by the user. Application type indicator control 1706 may correspond to application type indicator 1522 shown with reference to FIG. 15 after creation of the new alert rule.

In the example embodiment of FIG. 17, time delay control 1708 includes a text box user interface control in which the user may enter a time delay. Time delay control 1708 may be used to provide a delay associated with a repeated execution of the alert rule and possible repeated generation of an alert. A value entered using time delay control 1708 may correspond to a value indicated by delay indicator 1520 shown with reference to FIG. 15 after creation of the new alert rule. In an example embodiment, if no delay is entered in time delay control 1708, the default is immediate generation of the alert if the alert rule is satisfied. A second alert may not be generated unless the condition associated with the comparison is satisfied again after the time delay period. Thus, use of time delay control 1708 allows creation of an alert only if a test condition associated with a physiological characteristic is true and a specified period of time has passed to avoid alert fatigue.

In the example embodiment of FIG. 17, description control 1710 includes a text box user interface control in which the user may enter a description of the alert. A value entered using description control 1710 may correspond to the text field indicated by description 1518 shown with reference to FIG. 15 after creation of the new alert rule. A value entered using description control 1710 further may correspond to the text field indicated by alert description 1306 shown with reference to FIG. 13 after creation and generation of an alert based on the new alert rule.

In the example embodiment of FIG. 17, action control 1712 includes a text box user interface control in which the user may enter a proposed response to the alert or a possible cause of the alert generation. A value entered using action control 1712 further may correspond to the text field indicated by alert proposed action 1310 shown with reference to FIG. 13 after creation and generation of an alert based on the new alert rule.

Figure 19:
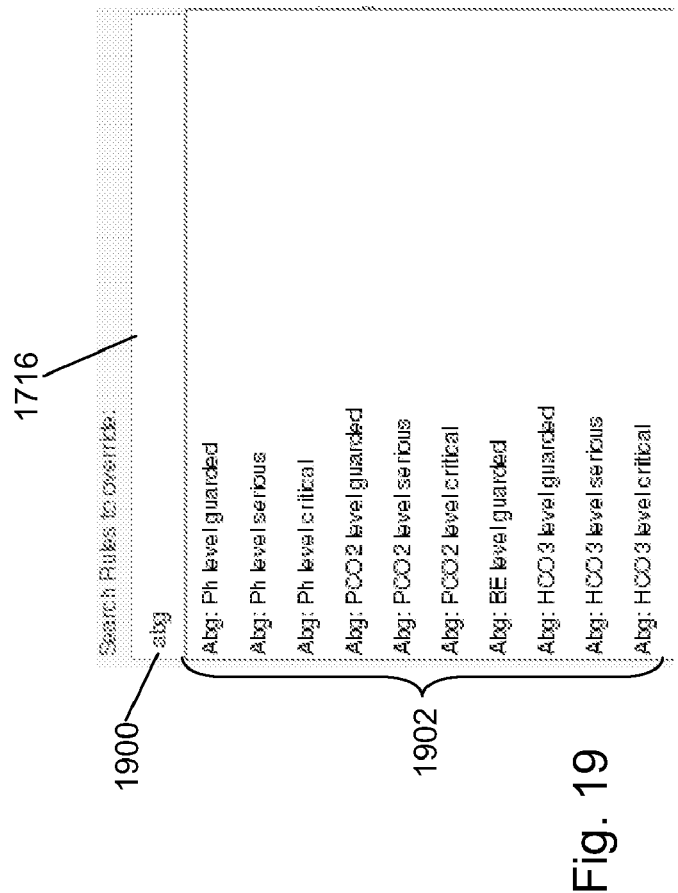

In the example embodiment of FIG. 17, rule override control 1714 presents a list of one or more alert rules, if any, which are overridden by the new alert rule. Rule override search control 1716 includes a drop down selector box user interface control into which the user may enter text and from which the user may select an alert rule to override. The alert rules from which the user may select are created based on matching the text entered by the user with an existing alert rule description. For example, with reference to FIG. 19, text 1900 entered in rule override search control 1716 causes creation of a list of alert rules 1902 having matching text in description 1518. Selection of an alert rule from the list of alert rules 1902 using rule override search control 1716 adds the selected alert rule and associated information to the list of one or more alert rules which are overridden by the new alert rule.

In the example embodiment of FIG. 17, rule evaluation control 1718 includes a check box which the user may select to indicate that evaluation of the rule should be repeated after expiration of a specified time period. Time control 1720 includes a text box in which the user may specify the repetition time period. Time units selector 1722 includes a drop down selector box user interface control from which the user may select a unit of time associated with the time value entered in the text box of time control 1720. For example, the drop down selector box may include units such as seconds, minutes, hours, days, weeks, etc.

Use of rule evaluation control 1718 allows a user to indicate that an alert rule be executed based on a set time period rather than based on when a measured value of the associated physiological characteristic is received. Additionally, use of rule evaluation control 1718 allows a user to define a rule based on a rate of change associated with a physiological characteristic. For example, the test condition may be related to an amount of change in the physiological characteristic and the use of rule evaluation control 1718 includes the time factor to determine a rate of change. Thus, the alert may be generated based on a rate of change and may cause generation of an alert even if all values are within normal limits because the measured value associated with the physiological characteristic is dropping at an alarming rate or percent based on the repetition time period specified using time control 1720.

In the example embodiment of FIG. 17, test condition control 1724 includes a text box in which the user may define an alert rule test condition 1725. Alert rule test condition 1725 may include a physiological characteristic indicator 1726 and a test condition 1728. In the example embodiment, of FIG. 17, alert rule test condition 1725 is written using an extensible markup language (XML) format. Of course, other controls may be used to allow the user to define the test condition executed such as a drop down selector box from which the user may select the physiological characteristic and one or more controls to allow the user to define the test condition. Alert rule test conditions involving multiple physiological characteristics can be defined. Additionally, alert rule test conditions involving a duration of the physiological characteristic falling within or without a specific range, above a threshold, and/or below a threshold may be defined. For example, alert rule test condition 1725 may include the following XML to define an alert rule that is satisfied if a heart rate is higher than 120 beats per minute for more than one hour and the blood pressure is higher than 80 in the last hour:

```
<condition>
    <and>
        <object name="r0">type='heart_rate' and value>
120</object>
        <notany by="r0rlm$crttime+(1/24)">
            <object name="r0">type='heart_rate' and value<
120</object>
            <object name="r0">type='bp' and value< 80</object>
        </notany >
    </and>
</condition>
```

Upon receipt of an indication of a user selection of save button 1730, the selected new alert rule is saved, for example, in an alert rules table of database 114, and new rule parameter list 1700 is removed from dashboard 636. Upon receipt of an indication of a user selection of cancel button 1732, the creation of a new alert rule is ignored, and new rule parameter list 1700 is removed from dashboard 636.

Figure 20:
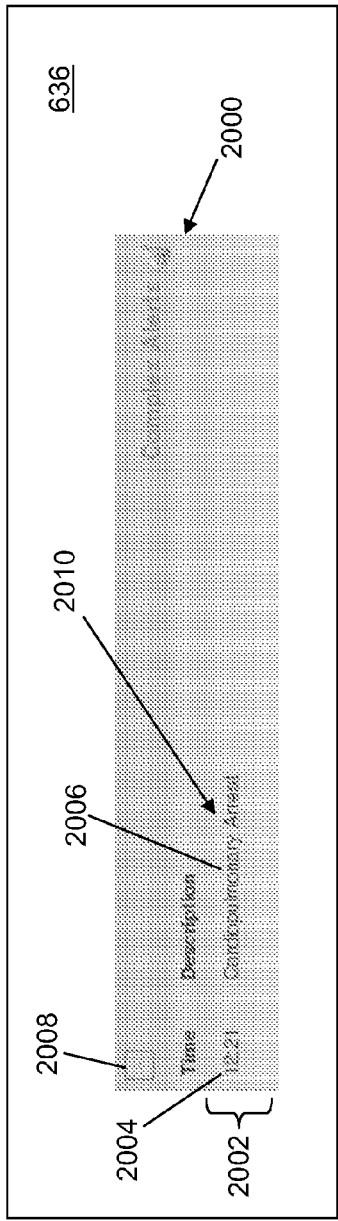

Upon receipt of the indication of the user selection of status button 616, dashboard space 636 may further include a complex alert status for the patient indicated in patient demographic information 604. For example, with reference to FIG. 20, dashboard space 636 may further include a complex alert status window 2000 presented under control of browser application 311 in combination with second medical alert application 310 and through interaction with medical alert application 210 at medical personnel alert device 104'. Complex alert status window 2000 may include one or more complex alerts 2002 generated based on execution of a complex alert rule. A complex alert rule may be generated based on execution of a plurality of alert rules and/or on an evaluation of a time during which one or more simple alert rule has been true. Thus, a complex alert rule may be based on alert rules of the one or more alert rules 1502 of alert rule list 1500 which may be referred to as simple alert rules.

In an example embodiment, the one or more complex alerts 2002 include a time value 2004 and a description 2006. Time value 2004 indicates the approximate time at which the measurement was taken based on which the complex alert was generated. Description 2006 provides an explanation as to why the complex alert is generated.

Complex alert status window 2000 also may include a collapse button 2008. Upon receipt of an indication of a user selection of collapse button 2008, complex alert status window 2000 may be collapsed to reduce the amount of space occupied by complex alert status window 2000 in dashboard 636. Upon receipt of an indication of a second user selection of collapse button 2008, complex alert status window 2000 may be expanded to again display the entire complex alert status window 2000 in dashboard 636.

Figure 21:
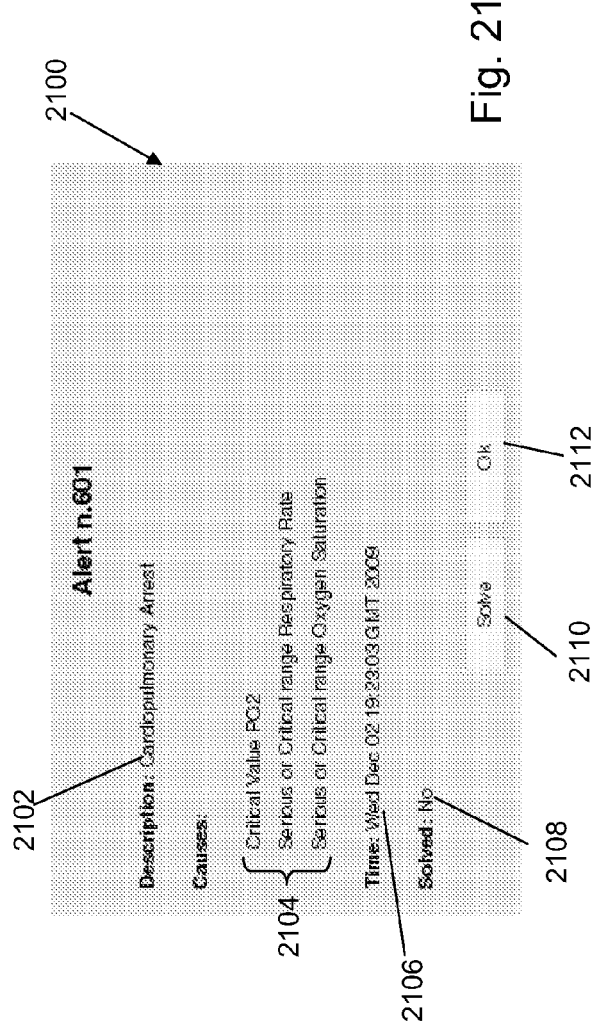

Upon receipt of an indication of a user selection of a complex alert of the one or more complex alerts 2002, a detailed description of the complex alert may be presented. For example, with reference to FIG. 21, a complex alert description window 2100 may be presented under control of browser application 311 in combination with second medical alert application 310 and through interaction with medical alert application 210 at medical personnel alert device 104' after receipt of an indication of a user selection of, for example, a cardiac arrest alert 2010. As known to a person of skill in the art, cardiac arrest alert 2010 may be selected by double-clicking on, for example, time value 2004 and/or description 2006 associated with cardiac arrest alert 2010.

Complex alert description window 2100 may include a complex alert description 2102, a complex alert cause 2104, a complex alert time and date 2106, a resolution indicator 2108, a solve button 2110, and an OK button 2112. Complex alert description 2102 includes a first text field describing the complex alert. In an example embodiment, the text field corresponds to description 2006 associated with cardiac arrest alert 2010. Complex alert cause 2104 includes a second text field summarizing the one or more physiological characteristics of the patient that caused generation of the complex alert. Complex alert time and date 2106 indicates the time that the complex alert was generated.

Resolution indicator 2108 indicates whether or not an action has been taken to resolve the complex alert. Upon receipt of an indication of a user selection of solve button 2110, a text box window may be opened to allow the user to enter an explanation of the action taken to resolve the complex alert. Upon receipt of an indication of a user closing the text box window, the explanation of the action taken to resolve the alert may be shown in resolution indicator 2108 and solve button 2110 may be removed from complex alert description window 2100. Upon receipt of an indication of a user selection of OK button 2112, complex alert description window 2100 is closed. Additionally, cardiac arrest alert 2010 may include a resolution indicator indicating that the complex alert has been resolved similar to that shown with reference to FIG. 12.

With reference to FIG. 22, dashboard space 636 may include a complex alert rule list 2200 presented under control of browser application 311 in combination with second medical alert application 310 and through interaction with medical alert application 210 at medical personnel alert device 104' after selection of "Cardiac Arrest" tab 1506. Complex alert rule list 2200 may include one or more complex alert rules 2202. Complex alert rule list 2200 may not be conveniently displayed in a single page. As a result, a page selector 2204 allows the user to select successive pages containing additional complex alert rules in complex alert rule list 2200.

Each complex alert rule of the one or more complex alert rules 2202 may include a priority level indicator 2208, a description 2210, and a delay indicator 2212. Priority level indicator 2208 indicates the condition priority level associated with the complex alert rule. For example, a priority may be indicated based on a color though other methods may be used including use of other numeric or alphanumeric values.

Delay indicator 2212 provides an indication of a delay associated with generation of the complex alert. For example, a time delay value associated with delay indicator 2212 may result in not generating the complex alert again until expiration of the time delay value after the last alert generation. The complex alert may not be generated unless the condition associated with the comparison is satisfied again after the time delay period.

Description 2210 includes a text field describing the complex alert. For example, description 2210 includes an indicator 2214 of the physiological characteristic to be compared and the test condition 2216 to which a measured value of the physiological characteristic is compared for a matching physiological characteristic. Test condition 2216 may include a determination related to the length of time that a physiological characteristic has satisfied another test condition such as a simple alert rule. For example, test condition 2216 may trigger a complex alert if a blood pressure of a patient has exceeded a threshold for more than 30 minutes. The blood pressure exceeding the threshold may be defined as an alert rule in alert rule list 1500.

If test condition 2216 is satisfied, the complex alert may be generated. In an example embodiment, however, priority level indicator 2208 represents a weight or urgency/seriousness associated with satisfaction of the complex alert rule, and a complex alert may be generated based on a number of complex alert rules that are true, on the weight or condition priority level associated with the complex alert rule(s) that are true, and/or on the time that has elapsed since the complex alert rule became true. For example, a complex alert may be generated when one "red" or serious condition priority level alert rule is true, when three "orange" or less serious condition priority level alert rules are true, when five "black" or still less serious condition priority level alert rules are true, etc. As a result, a single complex alert rule being true may not generate a complex alert. Thus, a trigger rule is also associated with a complex alert rule for a medical condition. For example, a trigger rule may include a plurality of rules. In an example embodiment, the plurality of rules may include: 1) one "red" or serious condition priority level alert rule being true triggers a complex alert; 2) three "orange" or less serious condition priority level alert rules being true triggers a complex alert; and 3) five "black" or still less serious condition priority level alert rules being true triggers a complex alert. In an example embodiment, a rule of the plurality of rules of the trigger rule may be based on a combination of alert rules having different condition priority levels. For example, a rule of the plurality of rules may include two "orange" or less serious condition priority level alert rules being true and three "black" or still less serious condition priority level alert rules being true triggers a complex alert. Of course, the rule may also be based on more complex Boolean logic such as greater than or equal to some number of priority level alert rules being true. Thus, a plurality of complex alert rules being true may be needed to generate a complex alert based on the condition priority level associated with each complex alert rule that is true. Groups of complex alert rules may be associated with a specific type of medical condition such as cardiac arrest, respiratory failure, renal failure, infection/sepsis, abdominal compartment syndrome, malnutrition, etc.

Figure 23:
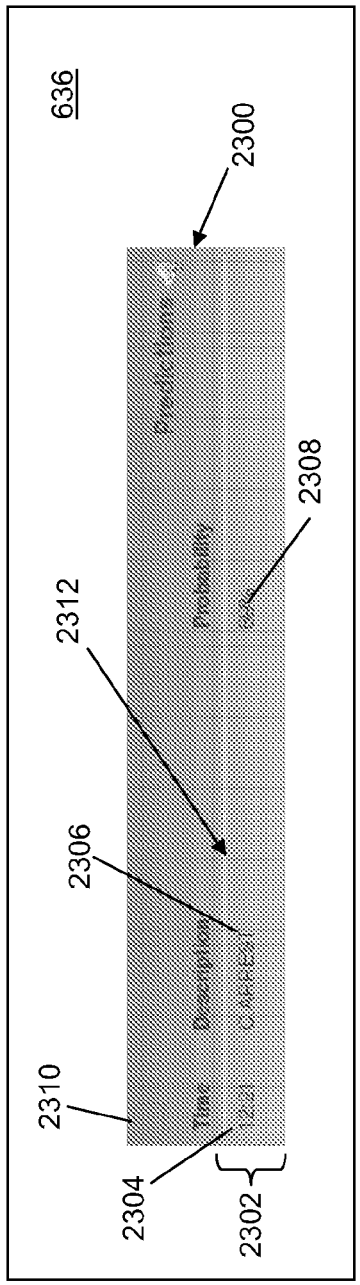

Upon receipt of the indication of the user selection of status button 616, dashboard space 636 may further include a prediction alert status for the patient indicated in patient demographic information 604. For example, with reference to FIG. 23, dashboard space 636 may further include a prediction alert status window 2300 presented under control of browser application 311 in combination with second medical alert application 310 and through interaction with medical alert application 210 at medical personnel alert device 104'. Prediction alert status window 2300 may include one or more prediction alerts 2302 generated based on execution of a prediction alert rule. A prediction alert rule may be generated based on data mining models that score the status of a patient for the probability of a risk situation such as for cardiac arrest or respiratory failure. The data mining models can be triggered based on specific conditions that may be based on the most relevant physiological characteristics associated with the prediction of the situation or may be triggered based on a change in the values used by the model.

In an example embodiment, the one or more prediction alerts 2302 include a time value 2304, a description 2306, and a probability of occurrence 2308. Time value 2304 indicates the approximate time at which the measurement was taken based on which the prediction alert was executed. Description 2306 provides an explanation as to why the prediction alert is generated. Probability of occurrence 2308 indicates the probability that the condition indicated by description 2306 may occur in a time window associated with the calculation. For example, a probability of a cardiac arrest occurring in the next 24 hours calculated based on a prediction model.

Prediction alert status window 2300 also may include a collapse button 2310. Upon receipt of an indication of a user selection of collapse button 2310, prediction alert status window 2300 may be collapsed to reduce the amount of space occupied by prediction alert status window 2300 in dashboard 636. Upon receipt of an indication of a second user selection of collapse button 2310, prediction alert status window 2300 may be expanded to again display the entire prediction alert status window 2300 in dashboard 636.

Figure 24:
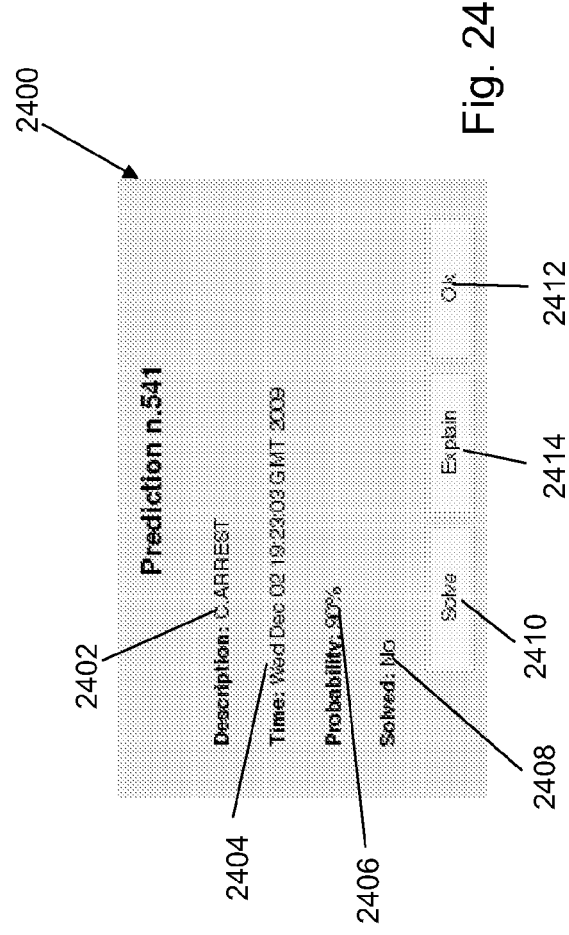

Upon receipt of an indication of a user selection of a prediction alert of the one or more prediction alerts 2302, a detailed description of the prediction alert may be presented. For example, with reference to FIG. 24, a prediction alert description window 2400 may be presented under control of browser application 311 in combination with second medical alert application 310 and through interaction with medical alert application 210 at medical personnel alert device 104' after receipt of an indication of a user selection of, for example, a cardiac arrest prediction alert 2312. As known to a person of skill in the art, cardiac arrest prediction alert 2312 may be selected by double-clicking on, for example, time value 2304, description 2306, and/or probability of occurrence 2308 associated with cardiac arrest prediction alert 2312.

Prediction alert description window 2400 may include a prediction alert description 2402, a prediction alert time and date 2404, a probability of occurrence 2406, a resolution indicator 2408, a solve button 2410, an OK button 2412, and an explain button 2414. Prediction alert description 2402 includes a first text field describing the prediction alert. In an example embodiment, the first text field corresponds to description 2306 associated with cardiac arrest prediction alert 2312. Prediction alert time and date 2106 indicates the time that the prediction alert was generated. Probability of occurrence 2406 includes a second text field describing the probability that the condition indicated by prediction alert description 2402 may occur in a time window associated with the calculation. In an example embodiment, the second text field corresponds to probability of occurrence 2308 associated with cardiac arrest prediction alert 2312.

Resolution indicator 2408 indicates whether or not an action has been taken to resolve the prediction alert. Upon receipt of an indication of a user selection of solve button 2410, a text box window may be opened to allow the user to enter an explanation of the action taken to resolve the prediction alert. Upon receipt of an indication of a user closing the text box window, the explanation of the action taken to resolve the alert may be shown in resolution indicator 2408 and solve button 2410 may be removed from prediction alert description window 2400. Upon receipt of an indication of a user selection of OK button 2412, prediction alert description window 2400 is closed. Additionally, cardiac arrest prediction alert 2312 may include a resolution indicator indicating that the prediction alert has been resolved similar to that shown with reference to FIG. 12.

Figure 25:
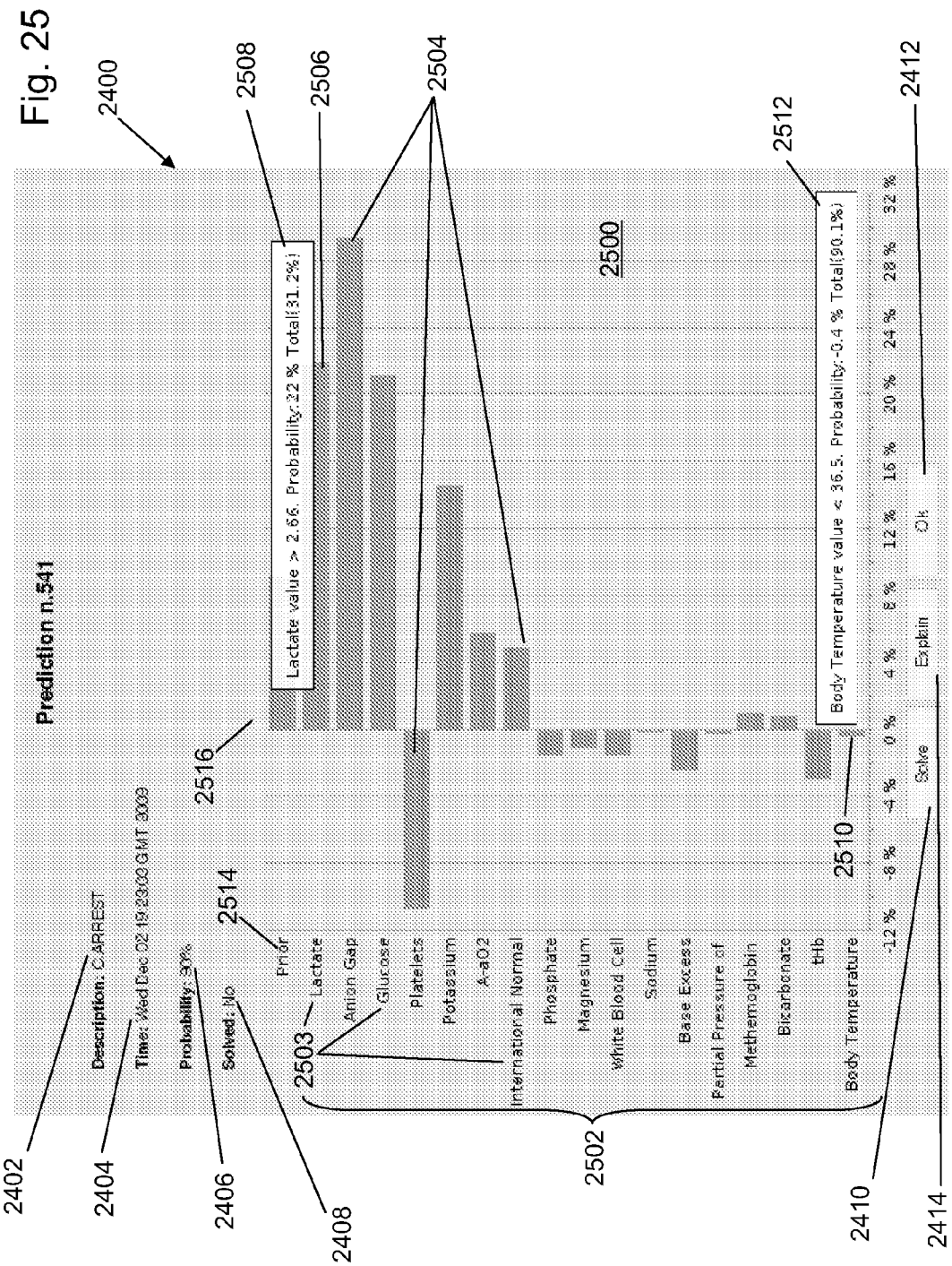

Upon receipt of an indication of a user selection of explain button 2414, prediction alert description window 2400 may be expanded to allow the user to review the physiological characteristics that contributed to the generation of cardiac arrest prediction alert 2312. For example, with reference to FIG. 25, prediction alert description window 2400 has been expanded to include a characteristics chart 2500. Characteristics chart 2500 may include a plurality of physiological characteristics 2502 which contributed to generation of cardiac arrest prediction alert 2312. Associated with each of the plurality of physiological characteristics 2502 is a characteristic indicator 2503 and a histogram bar 2504 indicating the contribution to probability of occurrence 2406 by the physiological characteristic indicated by characteristic indicator 2503. In the example embodiment, the physiological characteristic may have either a positive or a negative contribution (or essentially no effect) on the value associated with probability of occurrence 2406. For example, a negative or small histogram bar 2504 may indicate a normal value of the physiological characteristic; whereas, a positive or larger histogram bar 2504 may indicate an abnormal value of the physiological characteristic that contributes to the prediction of the condition such as a cardiac arrest. A cumulative contribution also may be shown.

By scrolling over histogram bar 2504, a summary window may present additional detail related to the physiological characteristic. For example, upon receipt of an indication of a user scrolling over a lactate histogram bar 2506, a lactate summary window 2508 may be presented. Lactate summary window 2508 may show the actual value of the most recently received value of the lactate, the contribution by the lactate measurement to the prediction of the condition, and the cumulative probability based on the previously considered physiological characteristics. Lactate summary window 2508 indicates that the lactate value is >2.66, the contribution to the probability of occurrence 2406 of the lactate value is 22%, and the cumulative probability of occurrence based on the previously considered physiological characteristics is 31.2%.

As another example, upon receipt of an indication of a user scrolling over a temperature histogram bar 2510, a temperature summary window 2512 may be presented. Temperature summary window 2512 may show the actual value of the most recently received value of the body temperature, the contribution to the prediction of the condition, and the cumulative probability based on the previously considered physiological characteristics. Temperature summary window 2512 indicates that the temperature value is <36.5, the contribution to the probability of occurrence 2406 of the temperature value is −0.4%, and the cumulative probability of occurrence based on the previously considered physiological characteristics is 90.1%. Because the body temperature is the last physiological characteristic considered, probability of occurrence 2406 is indicated as 90%.

In an example embodiment, probability of occurrence 2406 is determined using a Bayesian model to predict the probability of the occurrence of a condition. The Bayesian model may be built and trained by mining data in database 114 and executed using current patient data to predict an occurrence of the condition over a time window such as within the next 24 hours. The relevant physiological characteristics may be determined based on the mined data rather than based on the assumption of experts. After determining the relevant physiological characteristics based on data mining, thresholds associated with each physiological characteristic may be defined. A conditional probability associated with a value of each relevant physiological characteristic is calculated and added to the value determined for the other relevant physiological characteristics to determine the overall probability. Values associated with each relevant physiological characteristic need not be available. Additionally, the cumulative probability may be initialized to a non-zero value. For example, with reference to FIG. 25, an initial probability value is indicated with an indicator 2514 and an initial histogram bar 2516.

In an example embodiment, to train the Bayesian model, physiological characteristic values are collected, for example, in database 114. Patient-time window pairs are defined and training records with positive and negative instances of the condition such as cardiac arrest are created. Where the physiological characteristic values are numerical, representative maximum and minimum values within a time window are defined. Categorical or text physiological characteristic values may be excluded. The numerical attributes are discretized such that for low cardinality a greedy split is used and for high cardinality a logistic, regression-based split is used. Once discretized, the relevant physiological characteristics may be selected according to their association with the condition, for example, using a Fisher test based on p-value. As an example, the 25 physiological characteristics having the highest p-value may be selected as relevant. Other methods for selecting the relevant physiological characteristics may be used. For example, a minimum p-value may be used to indicate relevant as opposed to irrelevant physiological characteristics. The created Bayesian model can be stored in database 114 after creation.

To calculate a probability using the created Bayesian model, an execution of the prediction model is triggered, for example, based on generation of a complex alert. Values for the relevant physiological characteristics that are available for the patient are retrieved, for example, from database 114 and discretized for the most recent past time-window. Each relevant physiological characteristic measurement is input to the prediction model to calculate a probability. If the calculated probability exceeds a threshold, the prediction alert is generated.

With reference to FIG. 26, upon receipt of an indication of a user selection of change patient button 632, a list of patients 2600 of the user is displayed in dashboard space 636 under control of browser application 311 in combination with second medical alert application 310 and through interaction with medical alert application 210 at medical personnel alert device 104'. The list of patients 2600 may include one or more patients 2602. Each patient of the one or more patients 2602 may include a patient identifier 2604, patient demographic information 2606, a number of alerts indicator 2608, a number of complex alerts indicator 2610, and a number of prediction alerts indicator 2612.

Figure 27:
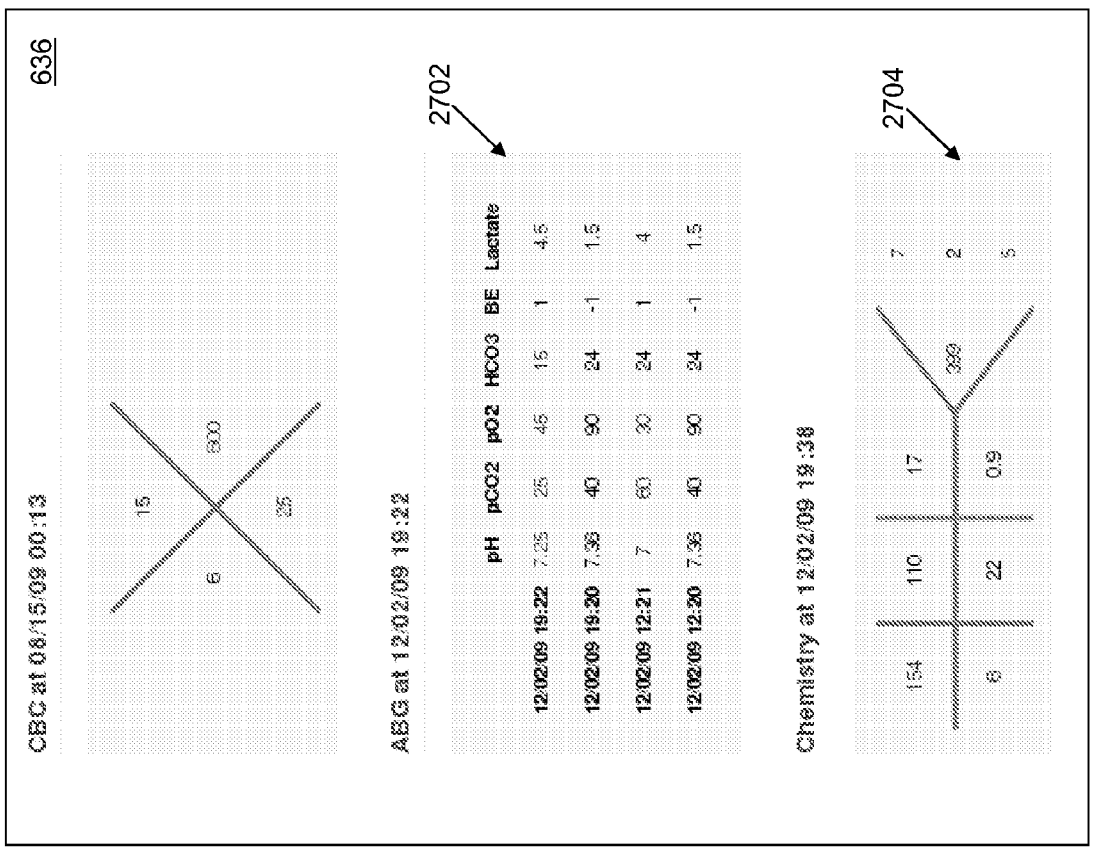

With reference to FIG. 27, upon receipt of an indication of a user selection of labs button 622, one or more graphs associated with lab results for the patient indicated in patient demographic information 604 are displayed in dashboard space 636 under control of browser application 311 in combination with second medical alert application 310 and through interaction with medical alert application 210 at medical personnel alert device 104'. The one or more graphs may include a complete blood count (CBC) chart 2700, an arterial blood gas (ABG) chart 2702, and a blood chemistry chart 2704. As known to a person of skill in the art, CBC chart 2700 may present the white blood cell count in a middle left position, the hemoglobin measurement in a top position, the hematocrit measurement in a middle right position, and the platelet count in a bottom position. ABG chart 2702 may present the results of an arterial blood gas test. Blood chemistry chart 2704 may include the results of a blood panel such as a sodium level, potassium level, chloride level, carbon dioxide level, blood urea nitrogen level, creatinine level, glucose level, calcium level, magnesium level, phosphorus. Color may be used to indicate a value that is out of a range such as a guarded, serious, or critical value.

Figure 28:
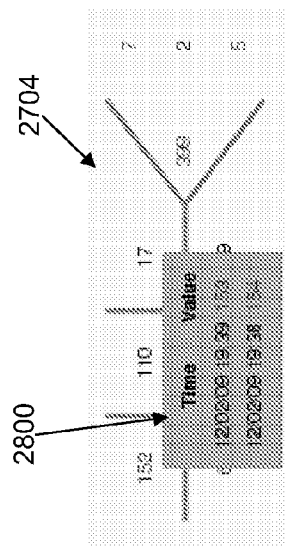

By scrolling over a value displayed in CBC chart 2700, ABG chart 2702, or blood chemistry chart 2704, a summary window may present additional detail related to the value. For example, upon receipt of an indication of a user scrolling over a value of blood chemistry chart 2704, a summary window 2800 may be presented as shown with reference to FIG. 28.

Summary window 2800 may show a history of previous measurements.

With reference to FIG. 29, upon receipt of an indication of a user selection of medication button 624, a list of medications 2900 of the patient indicated in patient demographic information 604 is displayed in dashboard space 636 under control of browser application 311 in combination with second medical alert application 310 and through interaction with medical alert application 210 at medical personnel alert device 104'. The list of medications 2900 may include one or more medications 2902. Each medication of the one or more medications 2902 may include a medication identifier 2904, a dosage indicator 2906, an application method 2908, a dosing schedule 2910, an adverse effects indicator 2912, a last given date/time indicator 2914, a starting date/time 2916, a stop date/time 2918, and a stop characteristic indicator 2920. Stop characteristic indicator 2920 may indicate a physiological characteristic that may indicate that use of the medication should be stopped.

Figures 30, 31:
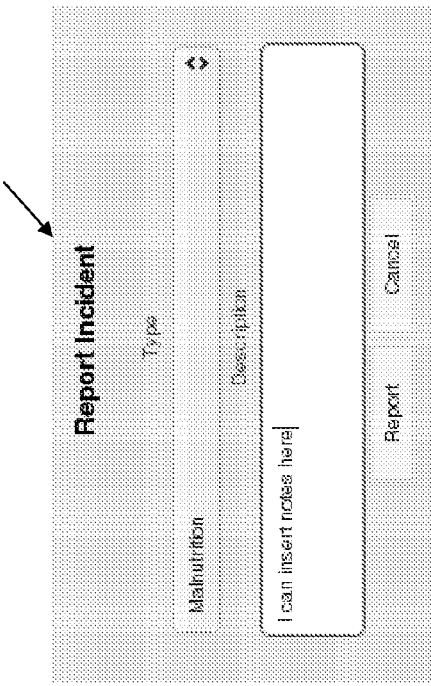

With reference to FIG. 30, upon receipt of an indication of a user selection of history button 628, a list of incidents 3000 of the patient indicated in patient demographic information 604 is displayed in dashboard space 636 under control of browser application 311 in combination with second medical alert application 310 and through interaction with medical alert application 210 at medical personnel alert device 104'. The list of incidents 3000 may include one or more incidents 3002. Each incident of the one or more incidents 3002 may include a date/time indicator 3004, an incident type indicator 3006, and an incident description 3008.

With reference to FIG. 31, upon receipt of an indication of a user selection of report incident button 634, a report incident window 3100 is displayed under control of browser application 311 in combination with second medical alert application 310 and through interaction with medical alert application 210 at medical personnel alert device 104'. Report incident window 3100 may include a type indicator control 3102 and an incident description indicator 3104. In an example, embodiment, type indicator control 3102 is a drop down selector box that allows the user to select the type of incident. In an example, embodiment, incident description indicator 3104 is a text field in which the user can enter a description of the incident. The date and time may be captured automatically so that the incident can be presented in the list of incidents 3000.

The word "example" is used herein to mean serving as an example, instance, or illustration. Any aspect or design described herein as "example" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise. The example embodiments may be implemented as a method, apparatus, or article of manufacture using standard programming and/or engineering techniques to produce software, firmware, hardware, or any combination thereof to control a computer to implement the disclosed embodiments.

The foregoing description of example embodiments have been presented for purposes of illustration and of description. It is not intended to be exhaustive or to limit the invention to the precise form disclosed, and modifications and variations are possible in light of the above teachings or may be acquired from practice of the invention. The functionality described may be implemented in a single executable or application or may be distributed among modules that differ in number and distribution of functionality from those described herein. Additionally, the order of execution of the functions may be changed depending on the embodiment. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system comprising:
a processor; and
a computer-readable medium operably coupled to the processor, the computer-readable medium having computer-readable instructions stored thereon that, when executed by the processor, cause the system to
(a) receive values for a plurality of physiological characteristics of a patient;
(b) compare the received values to a complex alert rule associated with a medical condition, wherein the complex alert rule comprises a plurality of alert rules, wherein each alert rule comprises an indicator of a physiological characteristic of a patient associated with the alert rule and a condition priority associated with an urgency of the alert rule, and further wherein the complex alert rule comprises a trigger rule, wherein the trigger rule includes a plurality of rules wherein each rule includes a number of satisfied alert rules for each value of the condition priority;
(c) determine a number of alert rules of the plurality of alert rules that are satisfied for each condition priority of the complex alert rule based on the comparison; and
(d) generate a complex alert if the determined number of alert rules for a condition priority satisfies the trigger rule of the complex alert rule.

2. The system of claim 1, further comprising repeating (b)-(d) for a plurality of complex alert rules.

3. The system of claim 2, wherein each of the plurality of complex alert rules is associated with a different medical condition.

4. The system of claim 2, wherein the trigger rule is the same for each of the plurality of complex alert rules.

5. The system of claim 1, wherein a rule of the plurality of rules of the trigger rule includes a number of satisfied alert rules for a single value of the condition priority.

6. The system of claim 1, wherein a rule of the plurality of rules of the trigger rule includes a number of satisfied alert rules for a plurality of values of the condition priority.

7. The system of claim 1, wherein the alert rule further comprises an alert value wherein a received value of the received values is compared to the alert value based on the indicator of the physiological characteristic to determine if the alert rule is satisfied.

8. The system of claim 7, wherein the alert value includes a maximum value wherein the alert rule is satisfied if the received value is above the maximum value.

9. The system of claim 8, wherein the alert value includes a minimum value wherein the alert rule is satisfied if the received value is below the minimum value.

10. The system of claim 7, wherein the alert value includes a minimum value wherein the alert rule is satisfied if the received value is below the minimum value.

11. The system of claim 1, wherein a received value of the received values is compared to the indicator of the physiological characteristic to determine if the alert rule is satisfied.

12. A non-transitory computer-readable medium having stored thereon computer-readable instructions that when executed by a computing device cause the computing device to:
- (a) receive values of a plurality of physiological characteristics of a patient;
- (b) compare the received values to a complex alert rule associated with a medical condition, wherein the complex alert rule comprises a plurality of alert rules, wherein each alert rule comprises an indicator of a physiological characteristic of a patient associated with the alert rule and a condition priority associated with an urgency of the alert rule, and further wherein the complex alert rule comprises a trigger rule, wherein the trigger rule includes a plurality of rules wherein each rule includes a number of satisfied alert rules for each value of the condition priority;
- (c) determine a number of alert rules of the plurality of alert rules that are satisfied for each condition priority of the complex alert rule based on the comparison; and
- (d) generate a complex alert if the determined number of alert rules for a condition priority satisfies the trigger rule of the complex alert rule.

13. The computer-readable medium of claim 12, further comprising repeating (b)-(d) for a plurality of complex alert rules.

14. The computer-readable medium of claim 13, wherein the trigger rule is the same for each of the plurality of complex alert rules.

15. The computer-readable medium of claim 12, wherein a rule of the plurality of rules of the trigger rule includes a number of satisfied alert rules for a single value of the condition priority.

16. The computer-readable medium of claim 12, wherein a rule of the plurality of rules of the trigger rule includes a number of satisfied alert rules for a plurality of values of the condition priority.

17. The computer-readable medium of claim 12, wherein the alert rule further comprises an alert value wherein a received value of the received values is compared to the alert value based on the indicator of the physiological characteristic to determine if the alert rule is satisfied.

18. The computer-readable medium of claim 17, wherein the alert value includes a maximum value wherein the alert rule is satisfied if the received value is above the maximum value.

19. The computer-readable medium of claim 12, wherein a received value of the received values is compared to the indicator of the physiological characteristic to determine if the alert rule is satisfied.

20. A method of generating a complex alert, the method comprising:
- (a) receiving values of a plurality of physiological characteristics of a patient;
- (b) comparing, by a processor of a computing device, the received values to a complex alert rule associated with a medical condition, wherein the complex alert rule comprises a plurality of alert rules, wherein each alert rule comprises an indicator of a physiological characteristic of a patient associated with the alert rule and a condition priority associated with an urgency of the alert rule, and further wherein the complex alert rule comprises a trigger rule, wherein the trigger rule includes a plurality of rules wherein each rule includes a number of satisfied alert rules for each value of the condition priority;
- (c) determining, by a processor of a computing device, a number of alert rules of the plurality of alert rules that are satisfied for each condition priority of the complex alert rule based on the comparison; and
- (d) generating, by a processor of a computing device, a complex alert if the determined number of alert rules for a condition priority satisfies the trigger rule of the complex alert rule.

* * * * *